| (12) United States Patent | (10) Patent No.: US 9,089,365 B2 |
| Jones et al. | (45) Date of Patent: Jul. 28, 2015 |

(54) TISSUE FIXATION DEVICE

(75) Inventors: Michael Jones, Chubbuck, ID (US); Nathan O. Plowman, Wellsville, UT (US); Nathan Erickson, Beaver Dam, UT (US); Andrew R. Fauth, River Heights, UT (US); Daniel J. Triplett, Providence, UT (US); Darin Ewer, Providence, UT (US); Jason M. Glad, Lewiston, UT (US)

(73) Assignees: IMDS LLC, Providence, UT (US); Mikenclaud LLC, Chubbuck, ID (US)

( * ) Notice: Subject to any disclaimer, the term of this patent is extended or adjusted under 35 U.S.C. 154(b) by 455 days.

(21) Appl. No.: 13/472,297

(22) Filed: May 15, 2012

(65) Prior Publication Data

US 2013/0289585 A1 Oct. 31, 2013

Related U.S. Application Data

(60) Provisional application No. 61/638,979, filed on Apr. 26, 2012.

(51) Int. Cl.
| A61B 17/03 | (2006.01) |
| A61B 17/42 | (2006.01) |
| A61B 17/08 | (2006.01) |
| A61B 17/122 | (2006.01) |
| A61B 17/44 | (2006.01) |
| A61B 17/00 | (2006.01) |
| A61B 17/34 | (2006.01) |

(52) U.S. Cl.
CPC ............. *A61B 17/4241* (2013.01); *A61B 17/08* (2013.01); *A61B 17/122* (2013.01); *A61B 17/42* (2013.01); *A61B 17/44* (2013.01); *A61B 17/442* (2013.01); *A61B 2017/00349* (2013.01); *A61B 2017/3488* (2013.01); *A61B 2017/4216* (2013.01); *A61B 2017/4225* (2013.01)

(58) Field of Classification Search
CPC .... A61B 17/442; A61B 17/08; A61B 17/122; A61B 17/42; A61B 17/4241; A61B 17/44; A61B 2017/4216; A61B 2017/4225
USPC .......................................... 606/209; 600/217
See application file for complete search history.

(56) References Cited

U.S. PATENT DOCUMENTS

| 75,158 A | 3/1868 | Hamilton |
| 496,711 A | 5/1893 | Thompson |
| 1,400,616 A * | 12/1921 | McCrory et al. .............. 600/217 |
| 1,462,202 A | 7/1923 | Hopper |
| 1,991,278 A | 2/1935 | Heintz |
| 2,082,782 A | 6/1937 | Allen |
| 2,108,206 A | 2/1938 | Meeker |

(Continued)

FOREIGN PATENT DOCUMENTS

| GB | 2305609 | 4/1997 |
| WO | WO9729889 | 8/1997 |

(Continued)

*Primary Examiner* — Jonathan W Miles
*Assistant Examiner* — Todd J Scherbel
(74) *Attorney, Agent, or Firm* — Maywood IP Law; Barbara Daniels; David Meibos

(57) ABSTRACT

Tissue fixation members interact with a housing to hold tissue relative to the housing and allow the orientation and position of the grasped tissue to be manipulated with improved efficacy. The tissue fixation members can be easily and quickly moved between deployed and retracted positions to reversibly grasp and release tissue.

12 Claims, 20 Drawing Sheets

(56) References Cited

U.S. PATENT DOCUMENTS

| | | |
|---|---|---|
| 2,146,472 A | 2/1939 | Heintz |
| 2,482,622 A | 9/1949 | Kahn |
| 2,536,145 A * | 1/1951 | Tapke .................... 606/205 |
| 2,616,421 A | 11/1952 | Martin |
| 3,877,433 A | 4/1975 | Librach |
| 4,022,208 A | 5/1977 | Valtchev |
| 4,085,756 A | 4/1978 | Weaver |
| 4,997,419 A | 3/1991 | Lakatos |
| 5,059,198 A | 10/1991 | Gimpelson |
| 5,100,382 A | 3/1992 | Valtchev |
| 5,209,754 A | 5/1993 | Ahluwalia |
| 5,259,836 A | 11/1993 | Thurmond |
| 5,336,228 A | 8/1994 | Cholhan |
| 5,368,598 A | 11/1994 | Hasson |
| 5,382,252 A | 1/1995 | Failla |
| 5,409,496 A | 4/1995 | Rowden |
| 5,445,643 A | 8/1995 | Valtchev |
| 5,464,409 A | 11/1995 | Mohajer |
| 5,520,698 A | 5/1996 | Koh |
| 5,540,700 A | 7/1996 | Rowden |
| 5,562,679 A | 10/1996 | Valtchev |
| 5,562,680 A | 10/1996 | Hasson |
| 5,578,048 A | 11/1996 | Pasqualucci |
| 5,643,285 A | 7/1997 | Rowden |
| 5,662,676 A | 9/1997 | Koninckx |
| 5,697,937 A | 12/1997 | Toma |
| 5,746,750 A | 5/1998 | Prestel |
| 5,833,611 A | 11/1998 | Tepper |
| 5,935,098 A | 8/1999 | Blaisdell |
| 5,980,534 A | 11/1999 | Gimpelson |
| 5,993,461 A | 11/1999 | Abae |
| 6,027,518 A | 2/2000 | Gaber |
| 6,371,973 B1 | 4/2002 | Tepper |
| 6,423,075 B1 | 7/2002 | Singh |
| 6,666,873 B1 | 12/2003 | Cassell |
| 7,175,634 B2 | 2/2007 | Van Heerden |
| 7,294,139 B1 | 11/2007 | Gengler |
| 7,325,546 B2 | 2/2008 | Burbank |
| 7,329,265 B2 | 2/2008 | Burbank |
| 7,479,145 B2 | 1/2009 | Burbank |
| D624,647 S | 9/2010 | Dionisi |
| 8,082,925 B2 | 12/2011 | McCartney |
| D653,338 S | 1/2012 | Mangeshikar |
| 8,162,954 B2 | 4/2012 | George |
| 2001/0021854 A1 | 9/2001 | Donnez |
| 2003/0187334 A1 | 10/2003 | Biswas |
| 2004/0236349 A1 | 11/2004 | Gellman |
| 2005/0080437 A1 | 4/2005 | Wright |
| 2005/0113854 A1 | 5/2005 | Uckele |
| 2005/0125006 A1 | 6/2005 | Nady |
| 2005/0251155 A1 | 11/2005 | Orban |
| 2005/0277948 A1 | 12/2005 | Cedars |
| 2005/0283188 A1 | 12/2005 | Loshakove |
| 2007/0142844 A1 | 6/2007 | Kotmel |
| 2007/0142860 A1 | 6/2007 | Kotmel |
| 2007/0173863 A1 | 7/2007 | Burbank |
| 2007/0260265 A1 | 11/2007 | Walter |
| 2007/0288051 A1 | 12/2007 | Beyer |
| 2008/0058833 A1 | 3/2008 | Rizvi |
| 2008/0109010 A1 | 5/2008 | Feuer |
| 2008/0154244 A1 | 6/2008 | Singh |
| 2008/0188863 A1 | 8/2008 | Chu |
| 2009/0105728 A1 * | 4/2009 | Noda et al. .................... 606/139 |
| 2009/0182329 A1 | 7/2009 | Dycus |
| 2009/0318914 A1 | 12/2009 | Utley |
| 2010/0106163 A1 | 4/2010 | Blair |
| 2010/0256623 A1 | 10/2010 | Nicolas |
| 2010/0274260 A1 | 10/2010 | D'Arpiany |
| 2010/0280524 A1 | 11/2010 | Lopez Zepeda |
| 2010/0305578 A1 | 12/2010 | Auerbach |
| 2011/0106116 A1 | 5/2011 | Ducharme |
| 2012/0029547 A1 | 2/2012 | Shelton |
| 2012/0109014 A1 | 5/2012 | Sherts |
| 2012/0109147 A1 * | 5/2012 | Auerbach et al. ............. 606/119 |
| 2013/0150877 A1 | 6/2013 | Ikeda |

FOREIGN PATENT DOCUMENTS

| | | |
|---|---|---|
| WO | WO2008136024 | 11/2008 |
| WO | WO2010114577 | 10/2010 |

* cited by examiner

TISSUE FIXATION DEVICE

CROSS-REFERENCE TO RELATED APPLICATIONS

This application claims the benefit of:

U.S. Provisional Patent Application No. 61/638,979 which was filed Apr. 26, 2012, entitled: TISSUE FIXATION DEVICE.

The above-identified document is herein incorporated by reference in its entirety.

BACKGROUND

The present disclosure includes examples of tissue fixation devices. Specifically, the tissue fixation devices described herein may be used with a uterine manipulator to grasp, retain and release cervical tissue. It will be appreciated that the disclosed embodiments may have applications outside of uterine manipulation, and may be used on other bodily tissues.

In some surgical procedures, it is desirable to control the position and orientation of an organ, such as a uterus, to help the surgeon operate on the uterus or on other parts of the body adjacent to the uterus. Uterine manipulator devices can be used to position and orient a uterus during surgery. U.S. Patent Application Publication No. US2012/0109147 discloses an example uterine manipulator system. Typical uterine manipulator systems consist of a bell-housing or cup shaped member that fits around the cervix and a rod member that is inserted through the cervix and into the uterus. The bell housing can be sized and shaped to compress the cervical tissue against the rod member to help the surgeon grasp the cervix and manipulate the position and orientation of the uterus. The bell housing can also provide a cutting guide to facilitate incision placement, for example colpotomy incisions and incisions requiring a safe distance from the ureters and uterine arteries. However, if the cervical tissue fixation within the bell housing is insufficient, a uniform colpotomy incision is difficult to achieve. Furthermore, the risk of damaging surrounding tissues, such as the ureters and uterine arteries, will increase if the tissue fixation is insufficient. The compressive forces imparted to the cervical tissue between the bell housing and the rod member are usually not sufficient enough to tightly grasp the cervix and ensure safe incision placement. Accordingly, it has been known to include a balloon in combination with the rod member which can be inflated inside of the uterus to provide additional pressure on the cervical tissue between the balloon and the bell housing to force the cervical tissue down into the bell housing and increase the gripping force of the bell housing on the cervix. However, the internal balloon may not create optimal tissue fixation, especially in patients with anatomical abnormalities, rigid tissues, scar tissue, and the like. Additionally, the balloon may leak or become accidentally "nicked" by other surgical instruments during the surgical procedure. This may result in loss of tissue fixation that can delay and complicate surgical incisions and/or removal of the uterus through the vagina in the case of a hysterectomy procedure. Moreover, it may not be desirable to use a balloon inside of a uterus containing cancerous cells, because the cancerous cells can be broken loose by the balloon and spread to other parts of the body. Sufficient tissue fixation is typically not achieved with a balloon, as is evidenced by workarounds currently used by many surgeons. For example, surgeons are known to use adjunctive stitches through the cervix which are then tied to the instrument to increase tissue fixation. This workaround adds additional steps to the surgery and further complicates things by making it difficult to quickly remove the bell housing and/or uterine manipulator from the patient if an emergency situation arises, such as the need to defibrillate the patient's heart.

Accordingly, it is desirable to provide a device that achieves reliable tissue fixation, with or without a balloon, that will last throughout the entire surgical procedure and that will not be compromised by rigid tissue, anatomical abnormalities, scar tissue, cancerous tissue, or the like. In some cases, it may also be desirable to generate tissue fixation close to certain incision sites, such as the colpotomy incision site, to increase the control, placement and precision of the incision. It is also desirable to provide a device that employs a simple actuation mechanism to quickly and easily engage and disengage the tissue fixation mechanism during surgery.

An example of the present technology disclosed herein includes a tissue fixation assembly shaped to be attached to a uterine manipulator. The assembly includes a housing, a fixation member carriage with deployable fixation members, and a cap. The fixation member carriage and fixation members are captured between the housing and the cap. In one example, a suture is attached to the fixation member carriage and is actuatable to move the fixation member carriage to deploy or retract the fixation members. The assembly may be inserted into a vagina and receive cervical tissue within the housing. The fixation members may then be deployed inwardly from the housing to grip the cervical tissue. The fixation members may also be locked in the deployed position to maintain the grip on the tissue. The fixation members may also be easily retracted to release the tissue and remove the device as needed.

Those of skill in the art will recognize that the following description is merely illustrative of the principles of the disclosure, which may be applied in various ways to provide many different alternative embodiments and may be applicable outside the fields of surgery or medical devices. While the present disclosure is made in the context of tissue fixation related to the cervix, for the purposes of illustrating the concepts of the design, it is contemplated that the present design and/or variations thereof may be suited to other uses for grasping any bodily tissue. Moreover, the devices and methods set forth herein may be used in open, percutaneous, and/or minimally invasive procedures.

All changes which come within the meaning and range of equivalency of the claims are to be embraced within their scope.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

BRIEF DESCRIPTION OF THE DRAWINGS

Various embodiments of the present disclosure will now be discussed with reference to the appended drawings. It will be appreciated that these drawings depict only typical examples of the present disclosure and are therefore not to be considered limiting of its scope.

DETAILED DESCRIPTION

Figure 1:
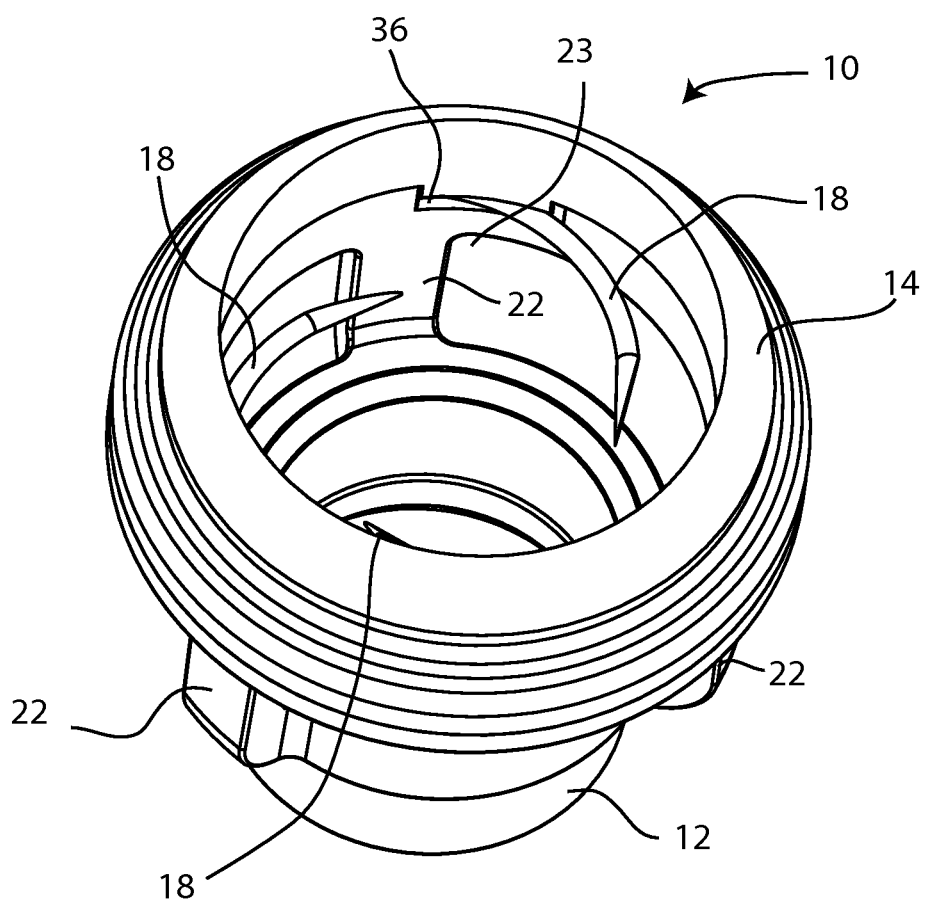
FIG. 1 is a perspective view of a tissue fixation device according to one example of the present disclosure having a housing, a cap, and deployable fixation members.
Figure 2:
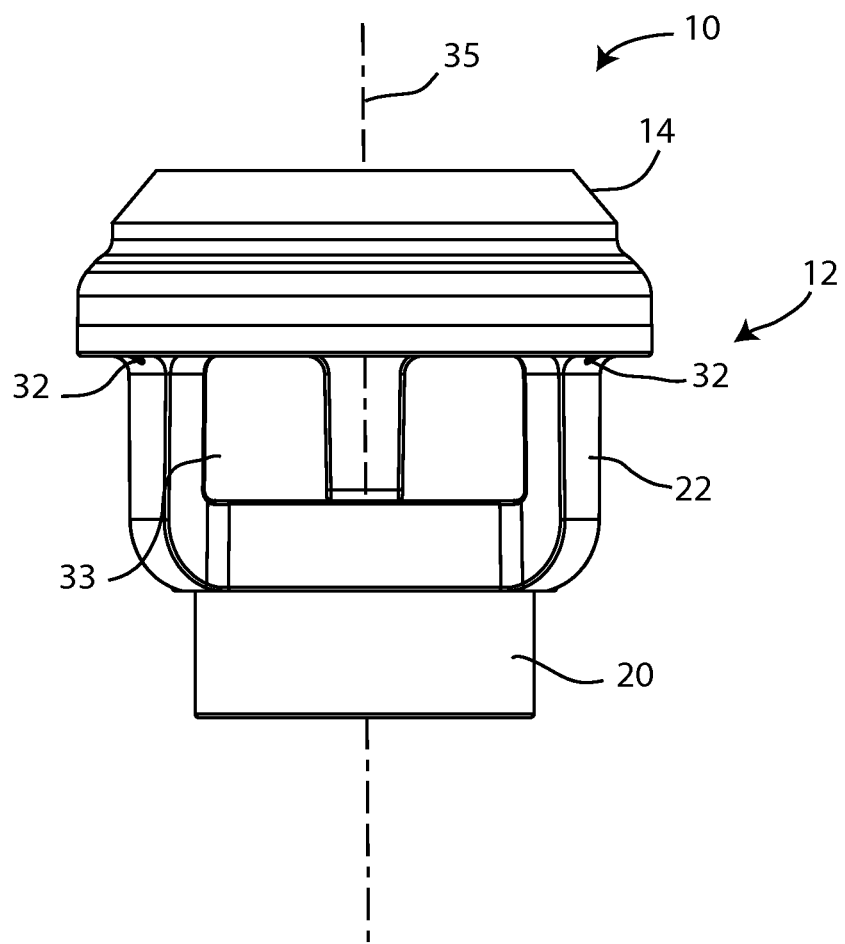
FIG. 2 is a side view of the tissue fixation device of FIG. 1.

While certain embodiments are shown and described in detail below by way of illustration only, it will be clear to the person skilled in the art upon reading and understanding this disclosure that changes, modifications, and variations may be made and remain within the scope of the technology described herein. Furthermore, while various features are grouped together in the embodiments for the purpose of streamlining the disclosure, it is appreciated that features from different embodiments may be combined to form additional embodiments which are all contemplated within the scope of the disclosed technology.

Not every feature of each embodiment is labeled in every figure in which that embodiment appears, in order to keep the figures clear. Similar reference numbers (for example, those that are identical except for the first numeral) may be used to indicate similar features in different embodiments.

Any of the devices described herein may be fabricated from metals, alloys, polymers, plastics, ceramics, glasses, composite materials, or combinations thereof, including but not limited to: titanium, titanium alloys, commercially pure titanium grade 2, ASTM F67, Nitinol, cobalt chrome, stainless steel, UHMWPE, PEEK, and biodegradable materials, among others. Different materials may be used within a single part. The devices disclosed herein may also encompass a variety of surface treatments or additives, including but not limited to: anti-microbial additives, analgesics, anti-inflammatories, etc. Any device disclosed herein may include a radiographic marker for imaging purposes. Any device disclosed herein may be color-coded or otherwise marked to make it easier for the surgeon to identify the type and size of the device.

FIGS. 1-8 illustrate one example of a tissue fixation device 10. The tissue fixation device 10 can include a housing 12, a cap 14, and a fixation member carriage assembly 16 (not visible in FIGS. 1 and 2) which carries at least one fixation member 18. In some examples, the fixation member 18 may be a needle. The fixation member carriage assembly 16 can be captured between the housing 12 and cap 14, and may be rotatable within a track 26 formed in the housing 12 and/or the cap 14. It is appreciated that in other embodiments, the cap 14 may be integral with the housing 12 and not formed as a separate element.

The cap 14 and housing 12 may be referred to as a bell cap or a bell housing, as they may form a bell shape in some examples. In some examples, the housing 12 can have at least one enclosed section that completely encloses at least one planar surface. The at least one planar surface can be defined by a cross-sectional plane through the housing that results in a planar surface that is completely enclosed by an open portion of the housing. In other words, the planar surface is an empty plane that is completely bounded by the housing 12. For example, with reference to FIG. 2, if a cross section of the housing 12 is taken perpendicular to the longitudinal central axis 35 and through the top portion of the housing, or the cap 14, a circular planar surface would be created which lies within the opening of the housing 12 and which is completely bounded by or surrounded by the housing 12 or cap 14. On the other hand, if the perpendicular cross-sectional plane were moved lower on the housing to where it crosses the struts 22, housing inner space 33, and windows 23, then this would result in a planar surface that is not completely bounded on all sides, or surrounded by the housing 12 because the windows 23 are open.

In other examples, the housing 12 may not have at least one enclosed section. In these examples there may be discontinuities or breaks in the housing (not shown) of any size or shape. In these examples, the at least one fixation member can be deployed away from an inner surface 42 of the housing and into the opening to grip tissue. The at least one fixation member can be also be retracted away from the opening toward an inner surface of the housing to release the tissue.

Figure 3A:
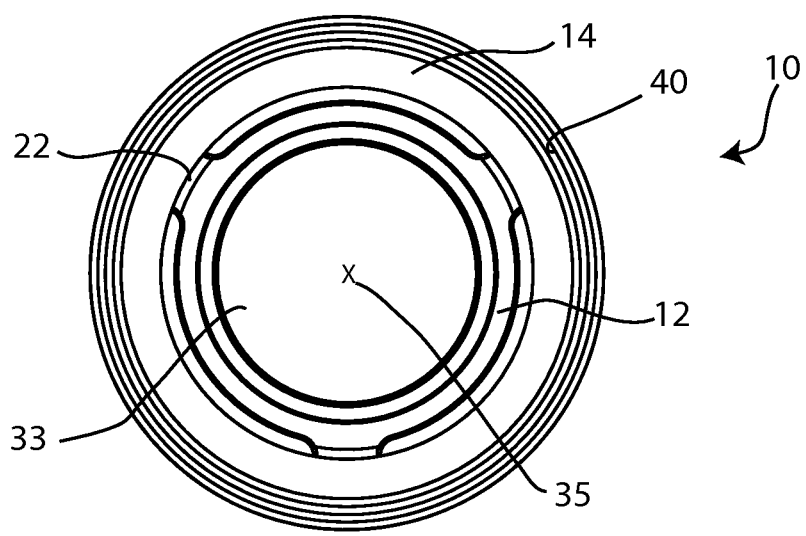
FIG. 3A is a top view of the tissue fixation device of FIG. 1 with the fixation members in a retracted position.
Figure 3B:
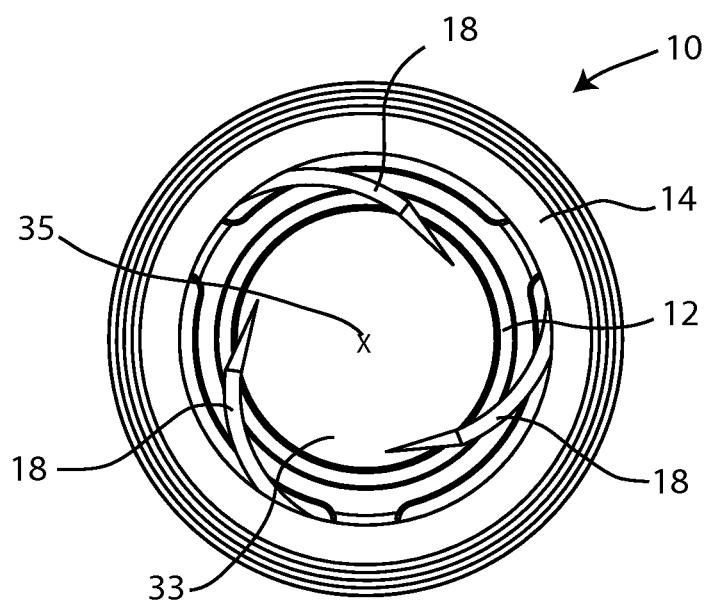
FIG. 3B is a top view of the tissue fixation device of FIG. 1 with the fixation members in a deployed position.

Referring to FIGS. 3A and 3B, the device can be actuable between a fixation member 18 retracted configuration, and a fixation member 18 deployed configuration. From the top or bottom perspective, the device can be radially symmetric. The embodiment shown in FIGS. 1-8 includes three curved fixation members 18. It will be appreciated that other embodiments may include more or fewer fixation members 18.

Figure 4:
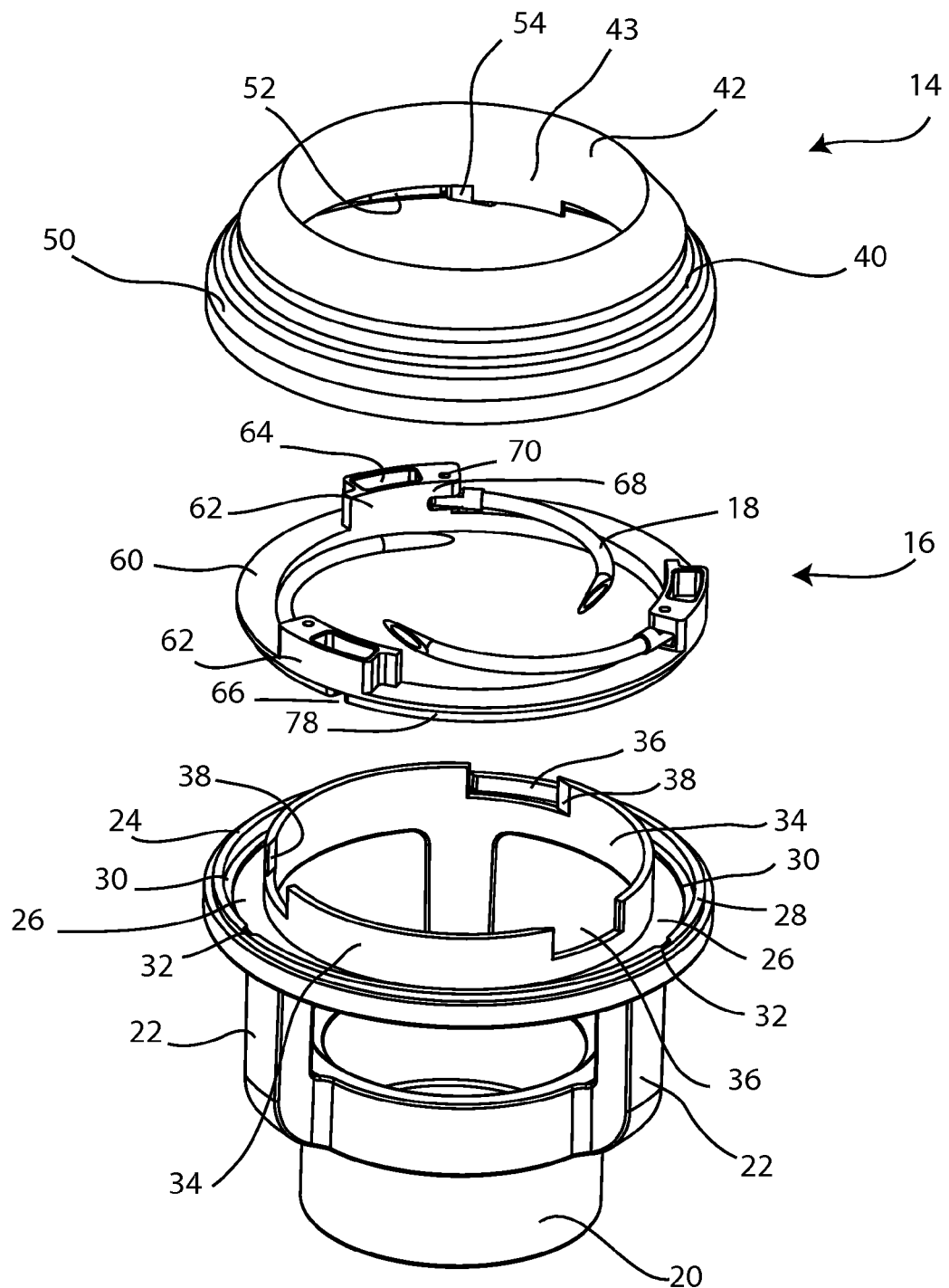
FIG. 4 is an exploded view of the tissue fixation device of FIG. 1.
Figure 5:
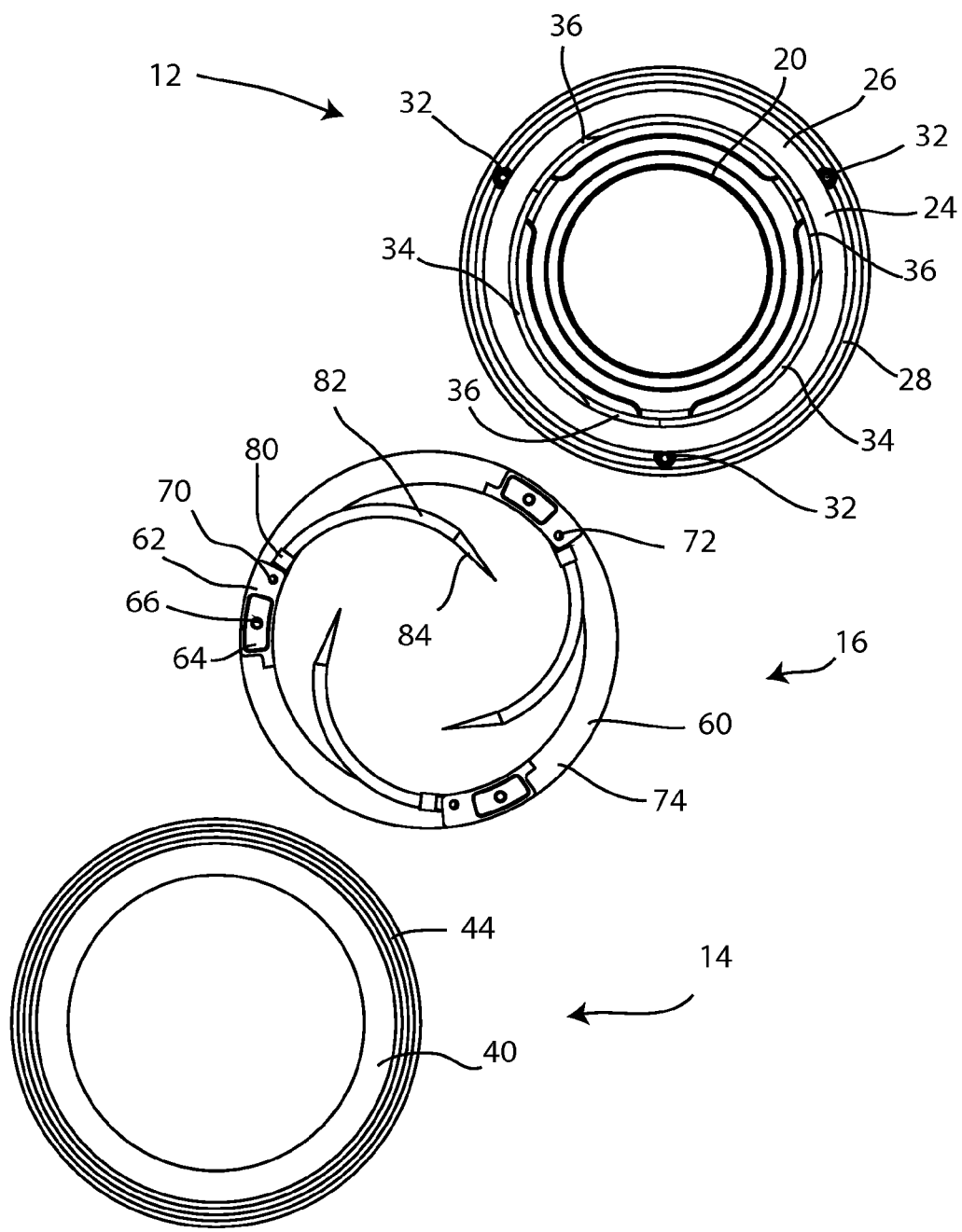
FIG. 5 is a top exploded view of the tissue fixation device of FIG. 1.

Referring to FIGS. 4 and 5, housing 12 can be substantially circular or cylindrical in shape. However, the housing 12 can also be conical, frustoconical, funnel, ovoid, or polygonal in shape, or any combination of shapes thereof. The shape of the housing is not as important as the ability of the housing to enclose tissue to be grabbed by one or more fixation members, as will be apparent from the present disclosure. Continuing with FIGS. 4 and 5, housing 12 may include an attachment portion 20 which may be shaped to connect to a uterine manipulator (not shown). A plurality of struts 22 can project superiorly from the attachment portion 20 and terminate at a carriage support 24. Windows 23 may be interspersed between the struts 22. However, in other embodiments, the housing may not include struts 22 or windows 23. The carriage support 24 can be ring-shaped, and include a carriage track 26, which may be substantially circular. An outer rim 28 can circumscribe the outer diameter of carriage track 26, and a step 30 may be formed intermediate the track 26 and the outer rim 28. One or more apertures 32 can open through the carriage support 24, and may pass through at least a portion of the outer rim 28 and step 30. A housing inner wall 34 can circumscribe the inner diameter of the carriage track 26, and may include a plurality of discontinuations, or wall gaps 36. At least one edge 38 of each wall gap 36 may be beveled. When operatively assembled, the fixation members 18 are deployable through the wall gaps 36; the beveled edges 38 may promote smooth deployment of the fixation members 18 and prevent the fixation members 18 from hanging up or being caught in the wall gaps 36.

Housing 12 may be generally stepped in outer profile, wherein the carriage support 24 has the widest outer diameter, struts 22 form a circle of intermediate diameter, and attachment portion 20 has the narrowest outer diameter. The inner wall 34, struts 22, and attachment portion 20, may surround and define a housing inner space 33. A lengthwise central axis 35 may extend through the housing inner space 33, also defined by the inner wall 34, struts 22, and attachment portion 20. The number and width of struts 22 and windows 23 may vary, and in some embodiments the housing 12 may be formed as a continuous piece extending between the attachment portion 20 and the carriage support 24, with no struts 22 or windows 23 present. The embodiment depicted in FIGS. 1-8 is generally bell shaped; however in other embodiments the housing 12 and/or the device 10 may have a cylindrical shape and may include a tapered portion at either end. In other embodiments the device 10 may be cup or bowl shaped, or polygonal.

Figure 6:
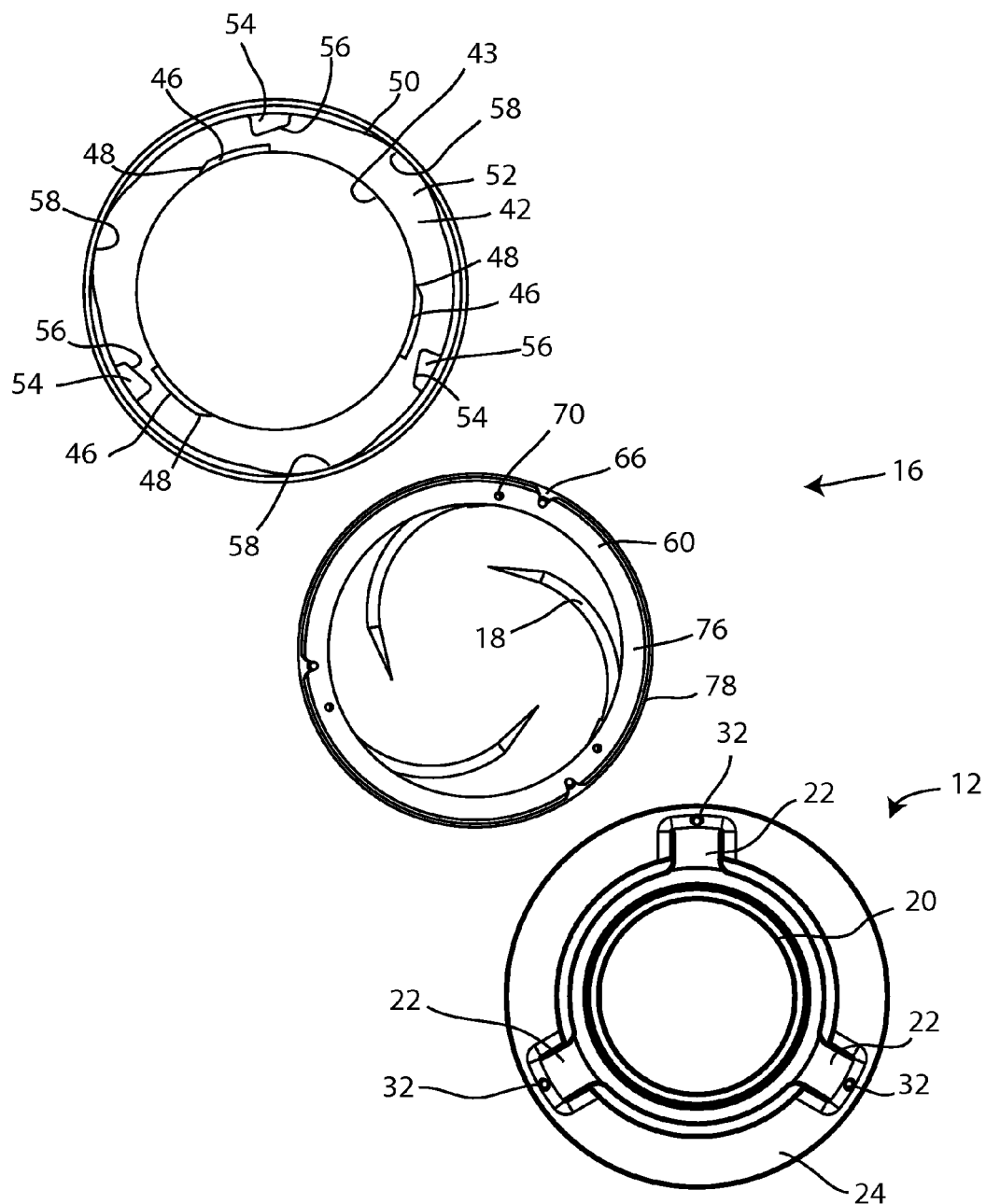
FIG. 6 is a bottom exploded view of the tissue fixation device of FIG. 1.

Cap 14 may have a ring-shape, and may include an outer side 40 opposite an inner side 42. An outer surface 44 of the outer side 40 may be positioned as an upper surface, and may include a plurality of steps, ridges and/or grooves which may facilitate gripping and manipulating the cap 14. As seen in FIG. 6, the inner side 42 may have circular outer and inner diameters. A cap inner wall 43 forms the inside diameter of the cap 14, and may include a plurality of tabs 46 which project inferiorly from the inner wall 43. Each tab 46 may include at least one beveled edge 48. A cap outer wall 50 may extend inferiorly, intermediate to and adjoining cap inner wall 43 and cap outer wall 50 and form a track cover 52. A plurality of cap bosses 54 can project inwardly from the cap outer wall 50. Each cap boss 54 may include a ramp feature 56 which urges the fixation member 18 inward as it is deployed. The cap 14 can also have beveled edges 48 which can also help urge the fixation member 18 inward as it is deployed. Cap outer wall 50 can include a plurality of recessed alcoves 58 which allow space for the curved fixation members 18 to be retained within the cap outer wall 50 when the fixation members 18 are in the retracted position. Housing 12 and cap 14 may be formed of plastic, or other materials listed herein.

Fixation carriage assembly 16 can include a generally circular fixation carriage 60. A plurality of mounting features 62 can project superiorly from the fixation carriage 60. Each mounting feature 62 may include a recess 64 through which an opening 66 is formed. Openings 66 can be sized to allow passage of a suture 90. Each mounting feature 62 can further include a fixation member mount 68. In the embodiment shown, fixation member mount 68 includes two pin holes 70 through which a mounting pin 72 passes. Fixation member carriage 60 can have a first or superior side 74 and a second or inferior side 76. A circular setback or groove 78 can be formed on the inferior side 76, and be sized to receive a suture.

Each fixation member 18 can be curved, rigid, and may terminate at a beveled point. The rigid fixation members may be formed of stainless steel, or other materials disclosed herein. Other embodiments may include flexible fixation members, which may be straight or curved, and may be made of Nitinol, for example. The fixation member curvature may be non-concentric with the curvature of the carriage track 26, for example the fixation member curvature may have a smaller diameter than the diameter of the carriage track. Each fixation member 18 may include a base portion 80, a shaft 82, and a point 84, which may also be referred to as a tip. The fixation may have an arch shape that lies substantially in a single plane in some examples, in other examples, the fixation member can be substantially straight. In yet further examples, the fixation member can have a curved shape in multiple planes or in an infinite number of planes. When assembled into the fixation member carriage assembly 16, base portion 80 is received in fixation member mount 68, and a mounting pin 72 may pass through the fixation member mount 68 and base portion 80 to form a hinge type connection, about which the fixation member 18 may pivot.

Figure 7A:
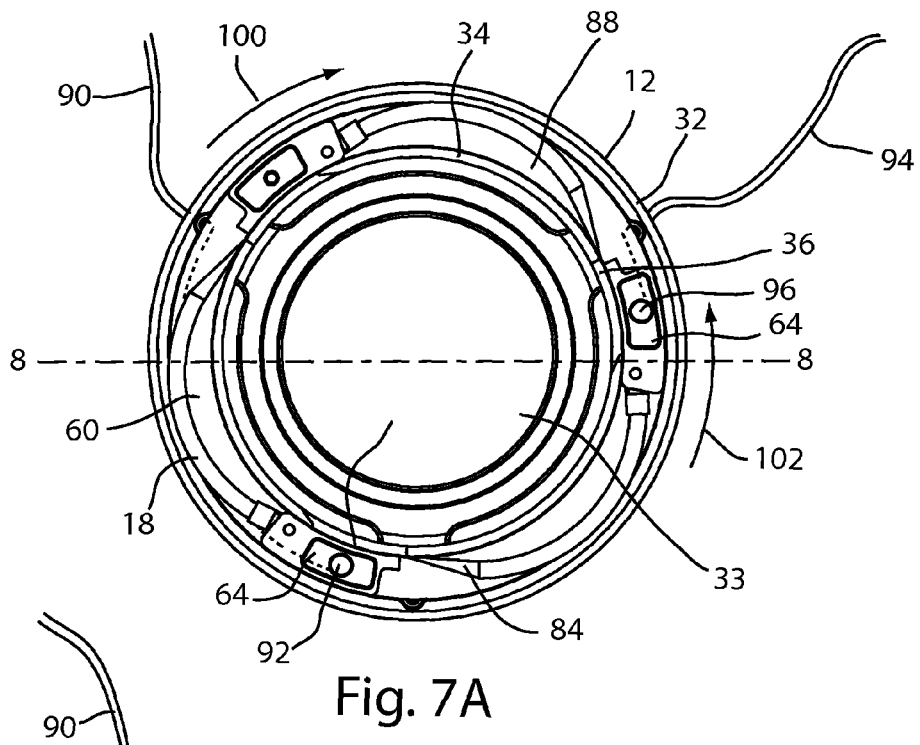
FIG. 7A is a top view of the housing and fixation member carriage assembly of the tissue fixation device of FIG. 1 with the fixation members in a retracted position and dashed lines indicating suture paths under the fixation member carriage assembly.
Figure 7B:
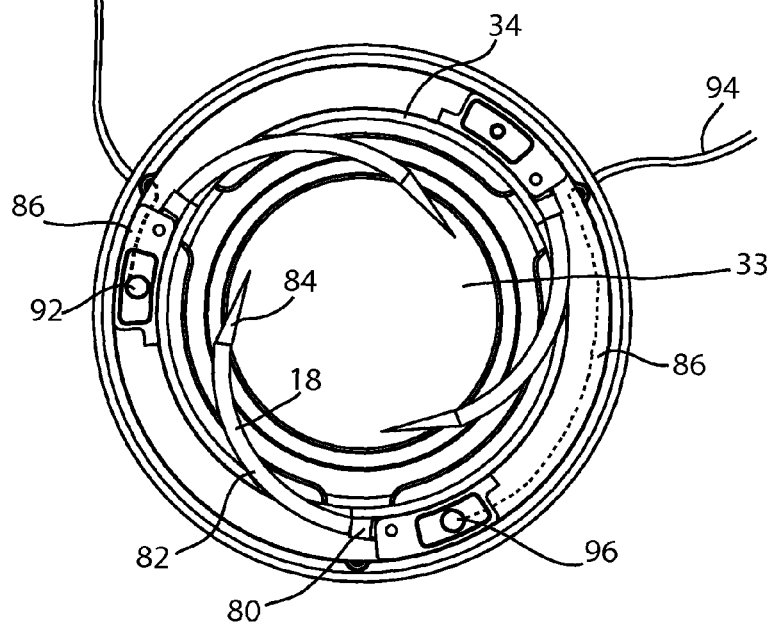
FIG. 7B is a top view of the housing and fixation member carriage assembly of the tissue fixation device of FIG. 1 with the fixation member in a deployed position.
Figure 8:
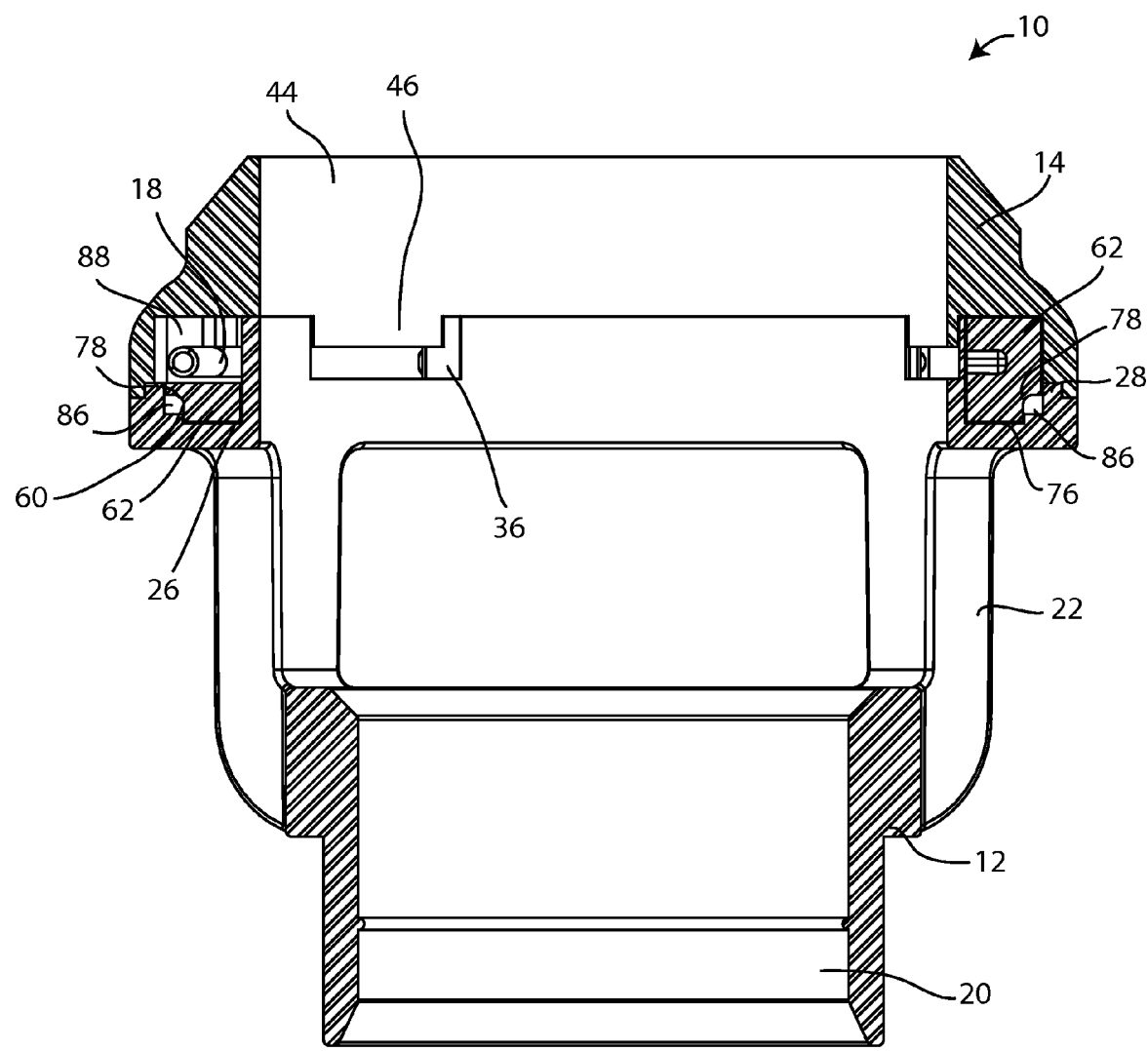
FIG. 8 is a side cross-sectional view of the tissue fixation device of FIG. 1 with the fixation members in a retracted position, taken along section line 8-8 in FIG. 7A.

Referring to FIGS. 7A, 7B, and 8, fixation member carriage assembly 16 may be mounted in the upper portion of housing 12, such that fixation member 60 is received in carriage track 26. A line gap or suture gap 86 may be formed between the groove 78 and outer rim 28. A first line, or suture 90 may be threaded through one opening 66, along suture gap 86 in a first direction 100 and through one aperture 32. A knot 92 may be formed in the suture end remaining at opening 66, the knot residing in recess 64 immediately adjacent opening 66, and the knot preventing withdrawal of the first suture through the opening 66. A second suture 94 may be threaded through a second opening 66, along suture gap 86 in a second direction 102 opposite the first direction, and through another aperture 32. The second suture 94 may also be knotted, forming knot 96 to prevent withdrawal. When the first and second sutures are thus placed, pulling on the first suture 90 will pull the fixation member carriage assembly 16 in the first direction 100, and pulling on the second suture will pull the fixation member carriage assembly 16 in the second, or opposite, direction 102. The sutures 90, 94 may be replaced by another type of line, flexible member, rigid member, filament, braid, yarn, cable, wire, chain, strap, lacing, or the like.

In an alternative threading embodiment, a single suture can be used. A first end of the suture is passed down through one opening 66, along suture gap 86 and out one aperture 32. The first end is then passed partially around the housing 12, up into a second aperture 32, along suture gap 86 and up through a second opening 66. The suture is knotted at both of the openings 66, and a length of suture is left along the housing 12, between the two openings 32. With this threading, pulling on one end of the length of suture will pull the fixation member carriage assembly 16 in one direction, and pulling on the second end of the length of suture will pull the fixation member carriage assembly 16 in the opposite direction.

The sutures or portions of the sutures may be color-coded. For example, the first suture may be colored green and the second suture may be colored red; of course any color scheme may be used so long as the sutures are visually distinct. Similarly, if one suture is used, different portions of the one suture may be color coded differently. In one example, the green color may be used to indicate that pulling on the green suture (or green portion) will deploy the fixation members and the red color may be used to indicate that pulling on the red suture (or red portion) will retract the fixation members. Also, portions of the suture(s) may be colored to a specific length in order to be used as visual indicators to show when the fixation members are fully deployed or retracted. For example, if all the red color is hidden because it has been drawn into the suture gap 86 that may provide indication that the fixation members are fully deployed. In some examples, only one suture, or one portion thereof, may be colored, a second portion or a second suture retaining its natural color.

In other embodiments, one or more sliding tabs, levers or other actuation features may be used instead of the sutures to move the fixation member carriage and/or deploy the one or more fixation members. The actuation features may push, pull or otherwise urge movement of the fixation member carriage and/or fixation members.

When the cap 14 is fitted to the housing 12, tabs 46 may fit into wall gaps 36, although inferior to each tab 46 an open portion of each gap can remain, the open portion sized to permit passage of the fixation member tip 84 and shaft 82. Fixation member carriage assembly 16 can thus be captured in an enclosure formed between the carriage track 26 and track cover 52. When the tissue fixation device 10 is in the retracted configuration, each fixation member 18 is substantially contained in a fixation member retention space 88 bounded by fixation member carriage 60, track cover 52, housing inner wall 34 and cap outer wall 50. In this configuration, each fixation member tip 84 is adjacent to, but not extending beyond, a wall gap 36. To move the device 10 into the deployed configuration, the appropriate suture is pulled, for example suture 90, and fixation member carriage assembly 16 will be pulled along carriage track 26 in direction 100. As the carriage assembly 16 travels, carrying fixation members 18, fixation member tips 84 will encounter ramp features 56 of bosses 54 and be forced, or deflected, through the open portions of wall gaps 36, thus being inwardly deployed. The deployment paths of fixation members 18 may be coplanar in some embodiments, and the fixation members 18 may be deployed along a plane perpendicular to a lengthwise central axis 35 of the housing 12. In other embodiments, the fixation members 18 may move up and/or down out of a plane perpendicular to a lengthwise central axis 35 of the housing 12. In these embodiments, the deployment paths of the fixation members 18 may be parallel to the central housing axis, or at an acute angle to the axis; the paths themselves may be nonlinear, curved, helical, or the like. The fixation members 18 may pierce tissue, such as cervical tissue, positioned in the housing inner space 33. Deployment can stop when the fixation member bases 80 become wedged between housing inner wall 34 and cap ramp feature 56. Another stop to the carriage motion may be formed when mounting feature 62 of the carriage assembly 16 encounters cap boss 54. Because of the wedging engagement of the fixation member bases between the housing 12 and cap 14, the deployed fixation members can be locked in the deployed configuration and remain deployed until they are intentionally retracted.

The fixation member tips 84 can be shaped similar to a hypodermic needle such that, minimum penetration force is needed to deploy the fixation members 18 into the tissue. Furthermore, in this example, when the three fixation members 18 are fully deployed, the fixation members 18 can engage with over 280 degrees of tissue, creating strong tissue fixation. Moreover, this embodiment allows the fixation members 18 to be close to the outer surface 44 of cap 14 which may serve as a cutting guide during colpotomy incisions. This allows the tissue fixation members to be less than about 0.25 inches from the cutting guide and the interiorly located fixation members 18 will not impinge on the cutting path. It will be appreciated that other size cutting guide tip designs can be made to adjust the distance and orientation of the cutting guide to achieve different incision placements as desired.

To move the device 10 into the retracted configuration, the second suture 92 is pulled. The fixation member bases 80 will be disengaged from the inner wall 34 and ramp feature 56, and fixation member carriage assembly 16 will be pulled in the opposite direction, or direction 102. As the carriage moves, the inner curved side of the shaft 82 of each fixation member will be forced outward as it encounters inner wall 34, and fixation members 18 will be retracted in through wall gaps 36.

Figure 9:
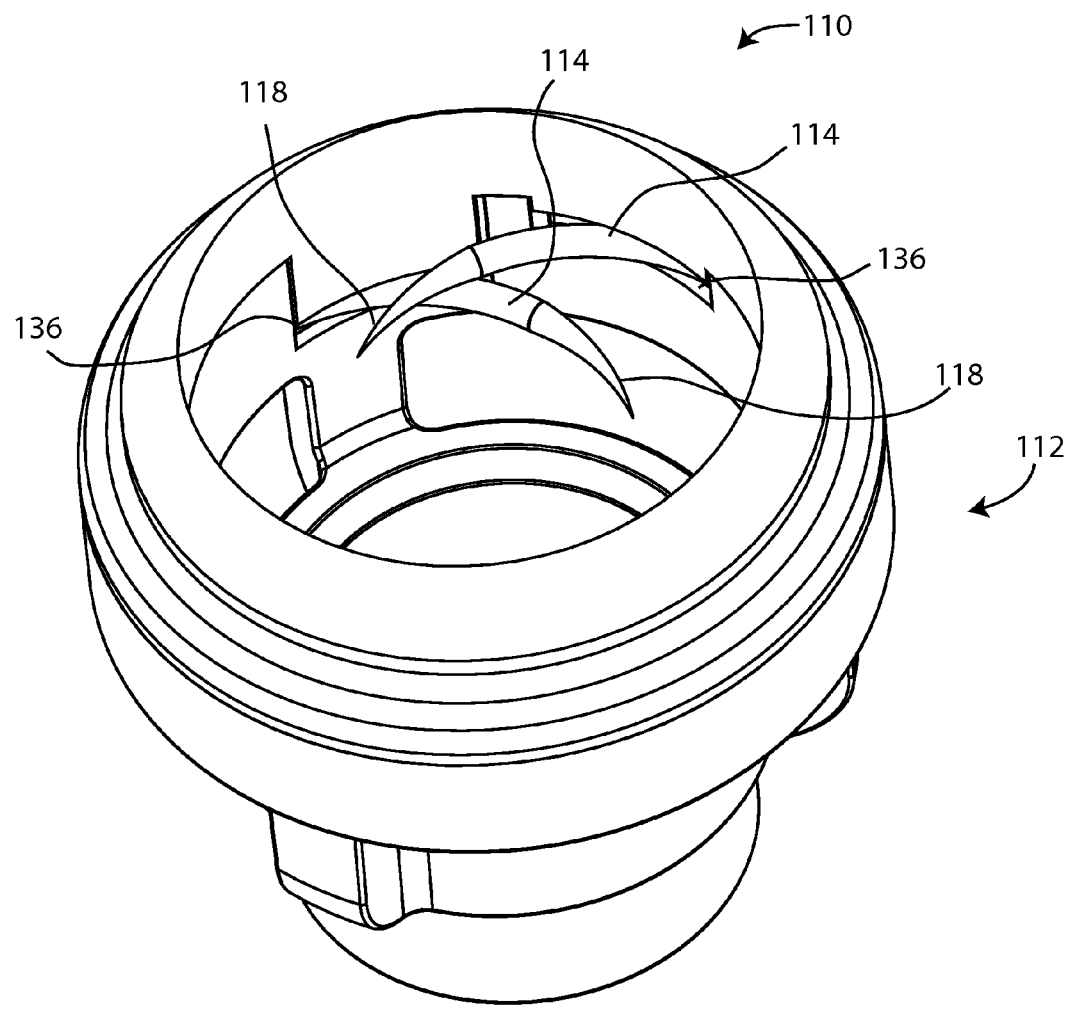
FIG. 9 is a perspective view of another tissue fixation device in accordance with the present disclosure with the tissue fixation members in the deployed configuration.
Figure 10:
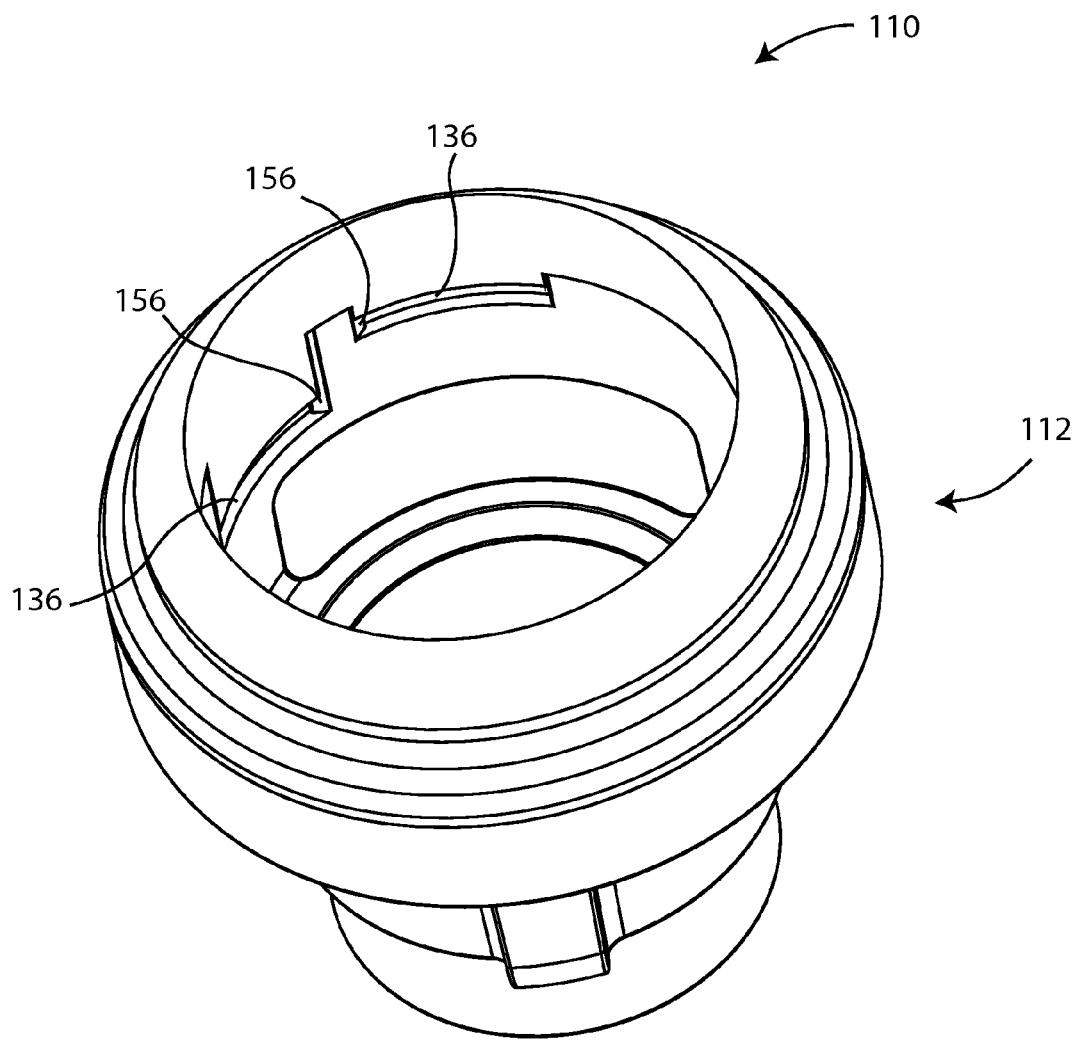
FIG. 10 is a perspective view of the tissue fixation device of FIG. 9 with the tissue fixation members in the retracted configuration.
Figure 11:
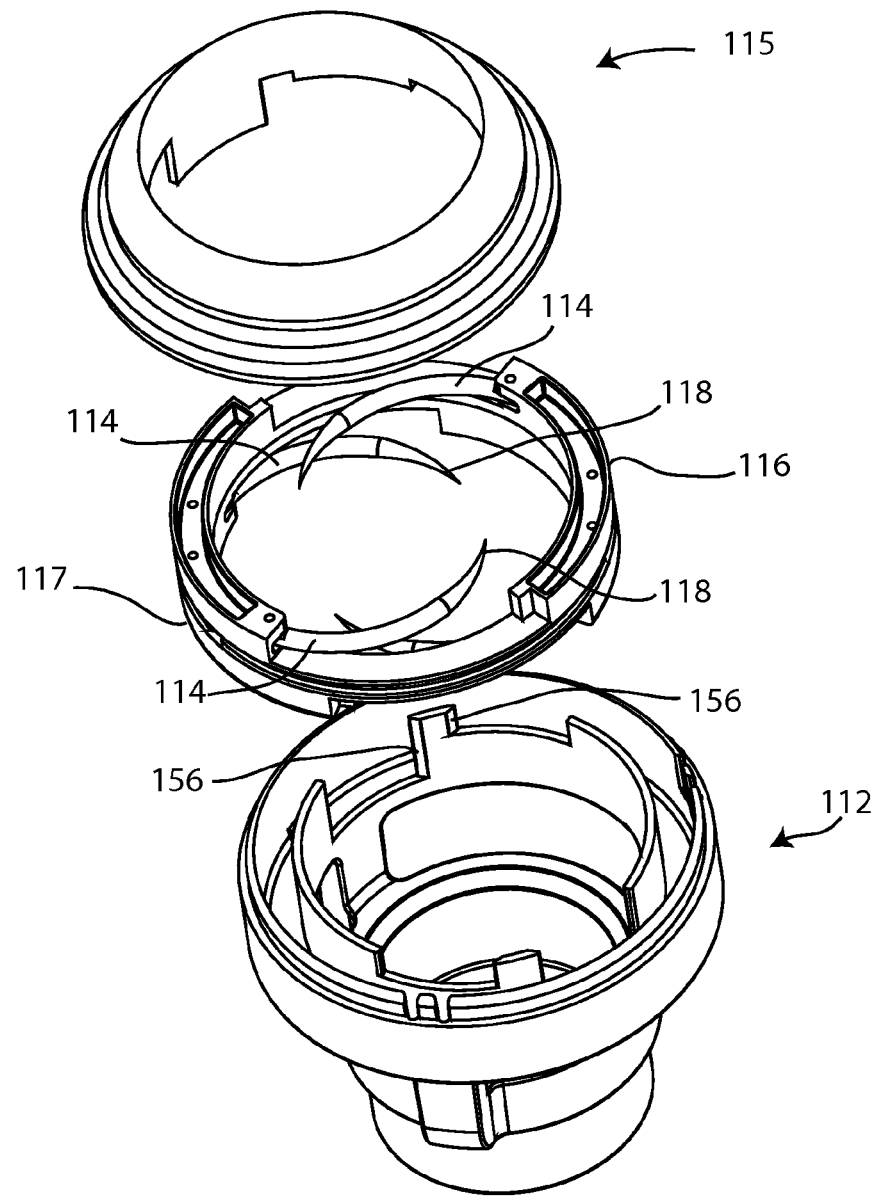
FIG. 11 is an exploded view of the tissue fixation device of FIG. 9.

FIGS. 9-20 show alternative embodiments of tissue fixation devices. FIGS. 9-11 show a tissue fixation device 110 having a housing 112, a cap 115, fixation member carriage 116 and at least two fixation members 114 which rotate into the deployed position in opposite directions. In this example, tissue fixation device 110 has four fixation members 114. Two of the fixation members rotate into the deployed position in the same direction and the other two fixation members rotate into the deployed position in the opposite direction. However, it will be understood that more or less fixation members 114 can be used in other embodiments without departing from the spirit or scope of the present disclosure. Similar to the example of FIGS. 1-8, the fixation members 114 can have beveled tips 118 which interact with ramp features (not shown) to force the fixation members inward toward the tissue as the fixation members 114 rotate into the deployed position, similar to other embodiments disclosed herein. The cap 115 can also have beveled edges 156 which may also help urge the fixation member 18 inward as it is deployed.

Operation of this tissue fixation device can be similar to that described above with reference to FIGS. 1-8, except that multiple fixation member carriages 116, 117 can be stacked on top of each other, with each of the fixation member carriages 116, 117 being free to rotate in opposite directions. In this example, two fixation member carriages 116, 117 are used. However, in other embodiments, more than two fixation member carriages can be used. Actuation of the fixation members 114 into the deployed position can be accomplished by any mechanical means disclosed herein. In one embodiment, a first suture (not shown) with one end split into two suture portions can be used with one of the split ends connected to the first fixation member carriage 116 in a first direction and the other split end connected to the second fixation member carriage 117 in a second direction. When the first suture is pulled, the two fixation member carriages 116, 117 will rotate in opposite directions relative to each other. A second suture (suture) with one end split into two suture portions can be used to reverse the rotation of the two fixation member carriages with the split ends of the second suture connected to the fixation member carriages 116, 117 in opposite directions relative to the split ends of the first suture. Thus, when the second suture is pulled, this causes the two fixation member carriages to rotate in opposite directions relative to pulling the first suture.

Figure 12:
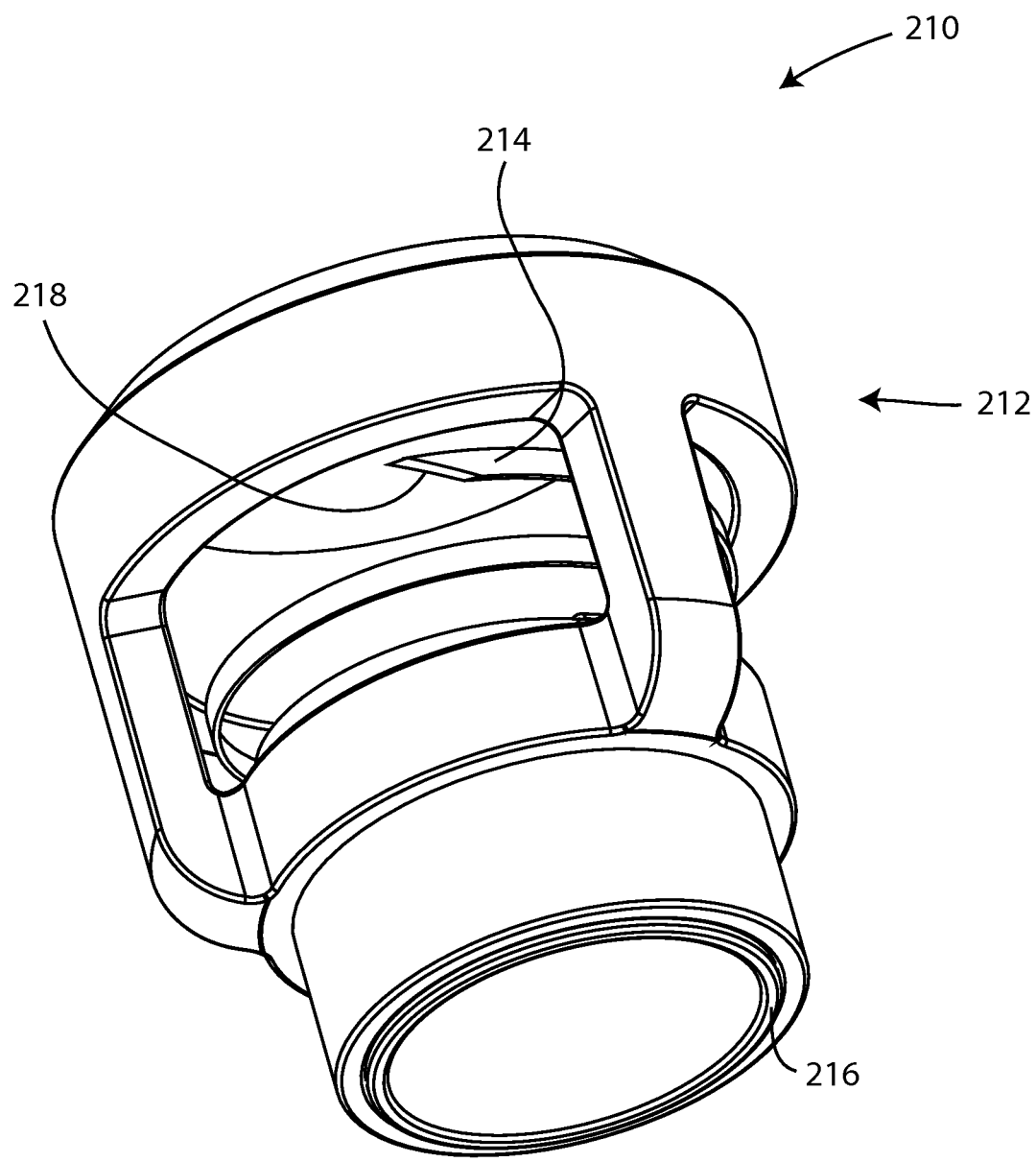
FIG. 12 is a perspective view of another tissue fixation device in accordance with the present disclosure with the tissue fixation member in the deployed configuration.
Figure 13:
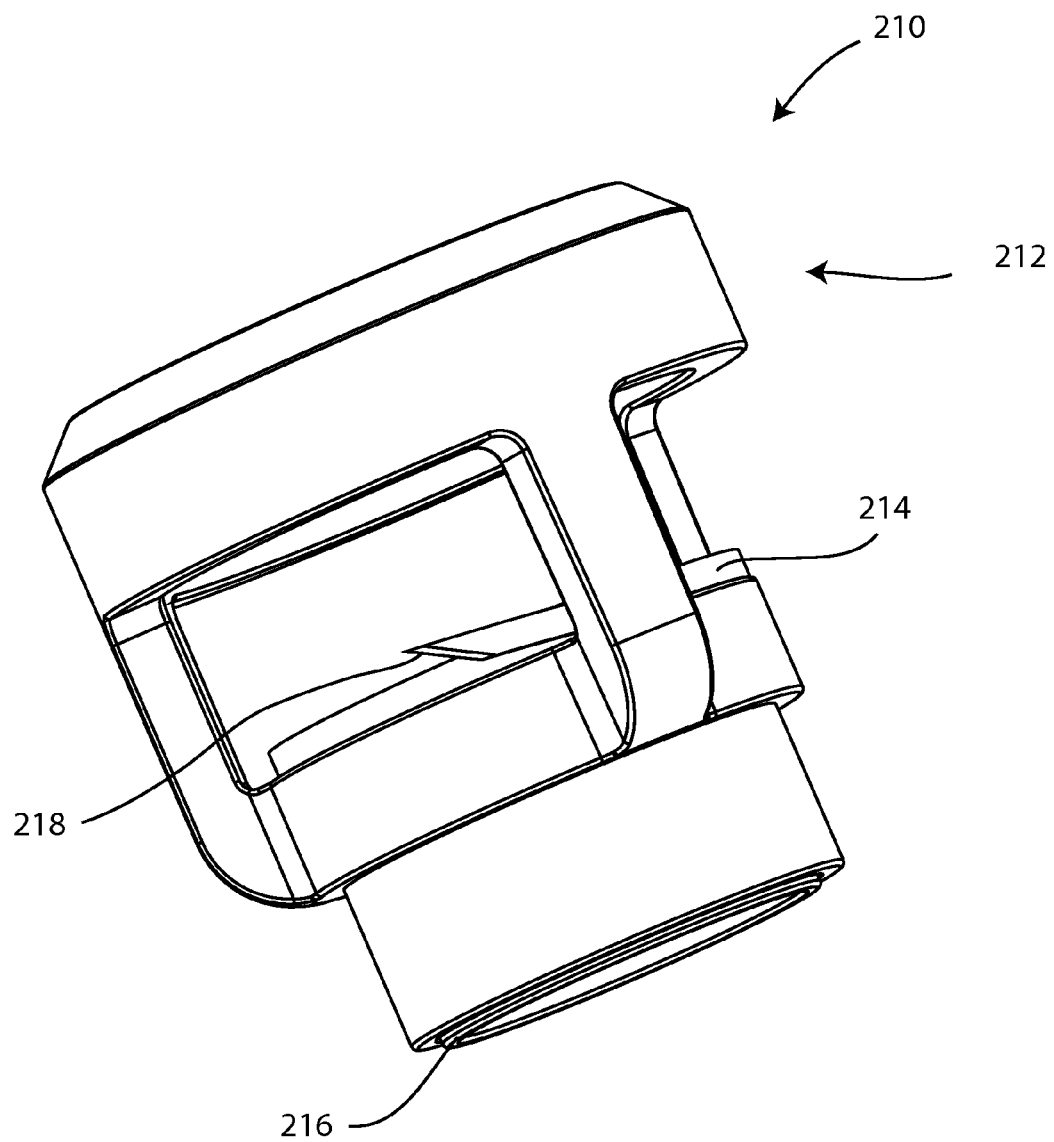
FIG. 13 is a perspective view of the tissue fixation device of FIG. 12 with the tissue fixation member in the retracted configuration.

FIGS. 12-13 show a tissue fixation device 210 having a housing 212, and a helical fixation member 214 which may be formed of a material such as Nitinol. FIG. 12 shows the helical fixation member 214 in the deployed position, and FIG. 13 shows the helical fixation member 214 in the retracted position. The helical fixation member 214 can be engaged with a rotatable carriage member 216. The helical fixation member can have a sharp beveled tip 218 that is angled upward toward the inserted tissue to help draw the fixation member 214 into the tissue as the fixation member is rotated into the deployed position.

In use, tissue may be received within housing 212, and the helical fixation member 214 can be rotatably advanced into the tissue by rotating carriage member 216 to engage and hold the tissue relative to the housing 212. It will be appreciated that helical fixation member 214 advances along a deployment path which includes a rotational component and an axial component relative to the center housing axis.

Figure 14:
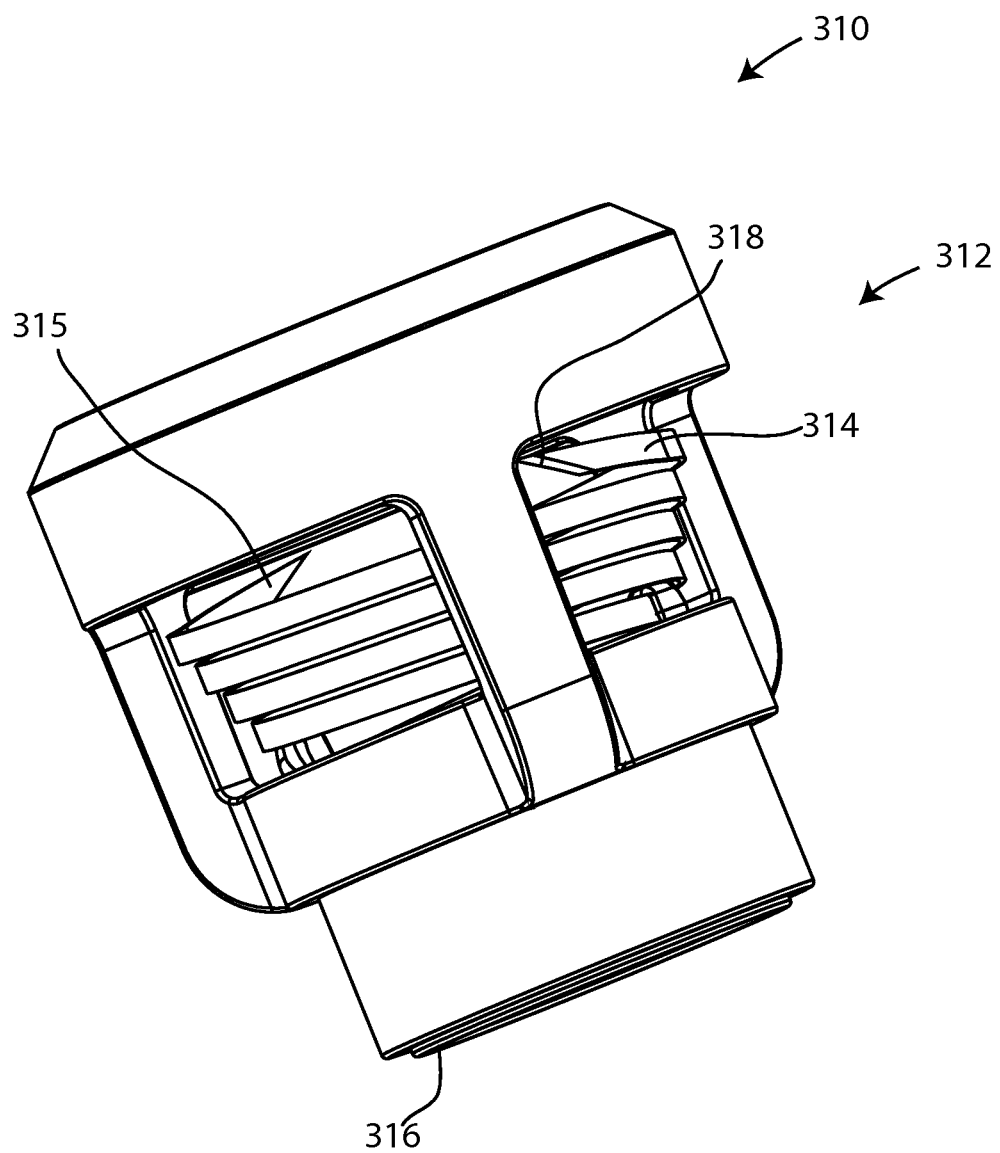
FIG. 14 is a perspective view of another tissue fixation device in accordance with the present disclosure with the tissue fixation members in the deployed configuration.
Figure 15:
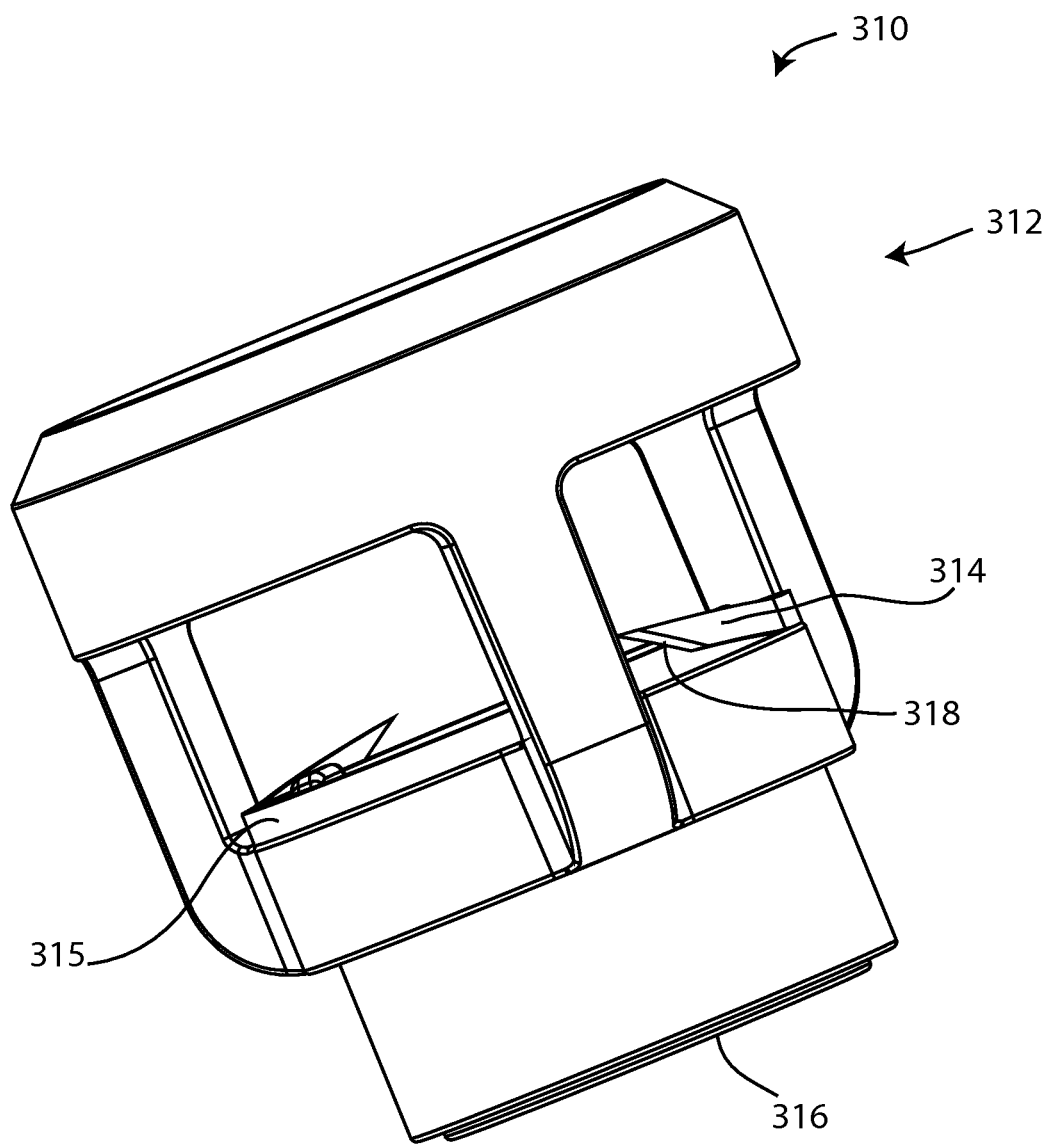
FIG. 15 is a perspective view of the tissue fixation device of FIG. 14 with the tissue fixation members in the retracted configuration.

FIGS. 14-15 show a tissue fixation device 310 having a housing 312, and multiple helical fixation members 314, 315 which may be formed of a material such as Nitinol. FIG. 14 shows the helical fixation members 314, 315 in the deployed position, and FIG. 15 shows the helical fixation members 314, 315 in the retracted position. The helical fixation members 314, 315 can be engaged with a rotatable carriage member 316. The helical fixation members 314, 315 can have sharp beveled tips 318 that are angled upward toward the inserted tissue to help draw the fixation members 314, 315 into the tissue as the fixation members 314, 315 are rotated into the deployed position. The sharp beveled tips 318 of each of the helical fixation members 314, 315 can be positioned out of phase with each other by 180 degrees.

In use, tissue may be received within housing 312, and the helical fixation members 314, 315 can be rotatably advanced into the tissue by rotating carriage member 316 to engage and hold the tissue relative to the housing 312. It will be appreciated that helical fixation members 314, 315 advance along a deployment path which includes a rotational component and an axial component relative to the center housing axis. It will be appreciated that other embodiments may include more than two helical fixation members without departing from the spirit or scope of the present disclosure.

Figure 16:
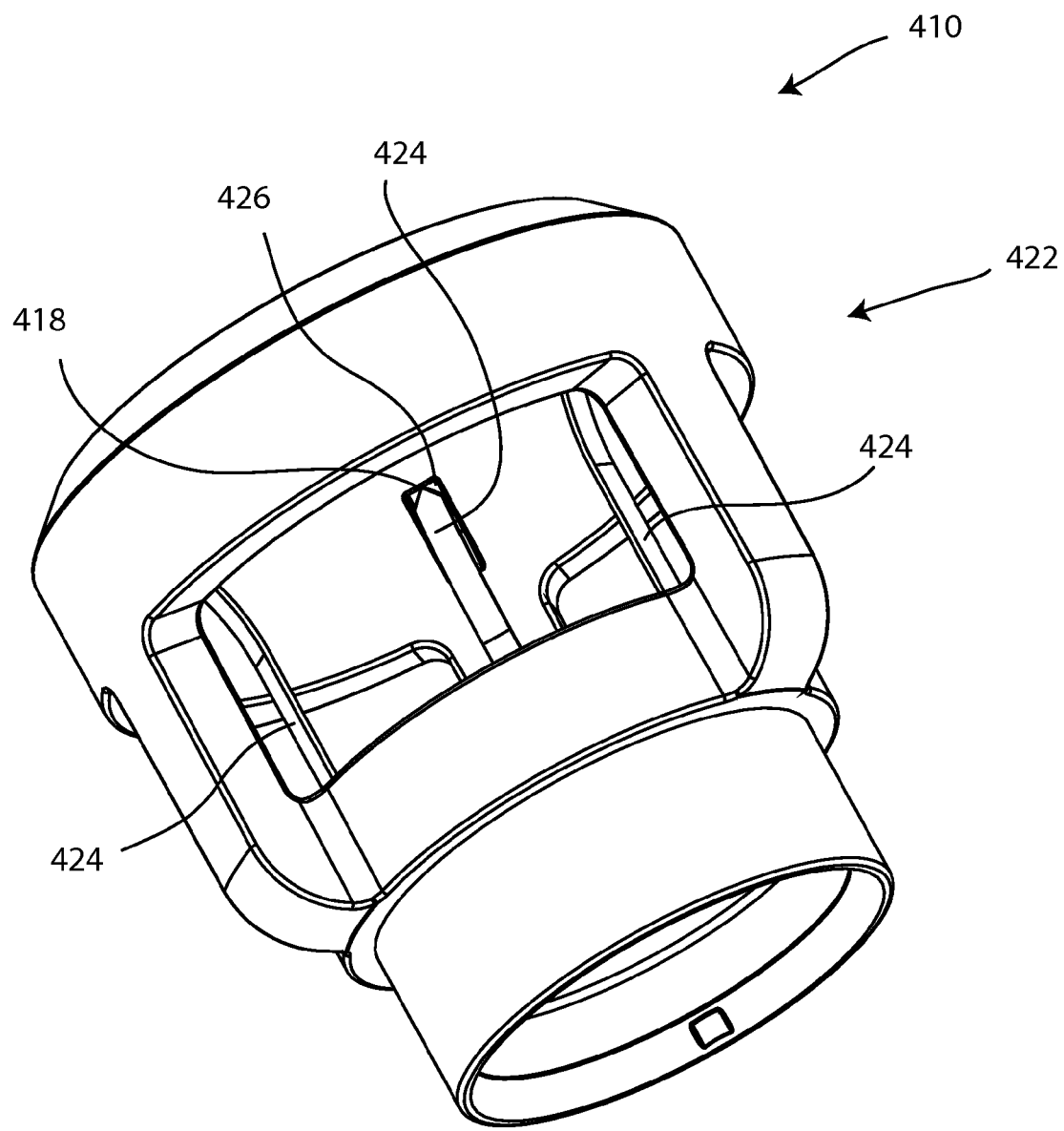
FIG. 16 is a perspective view of another tissue fixation device in accordance with the present disclosure with the tissue fixation members in the deployed configuration.
Figure 17:
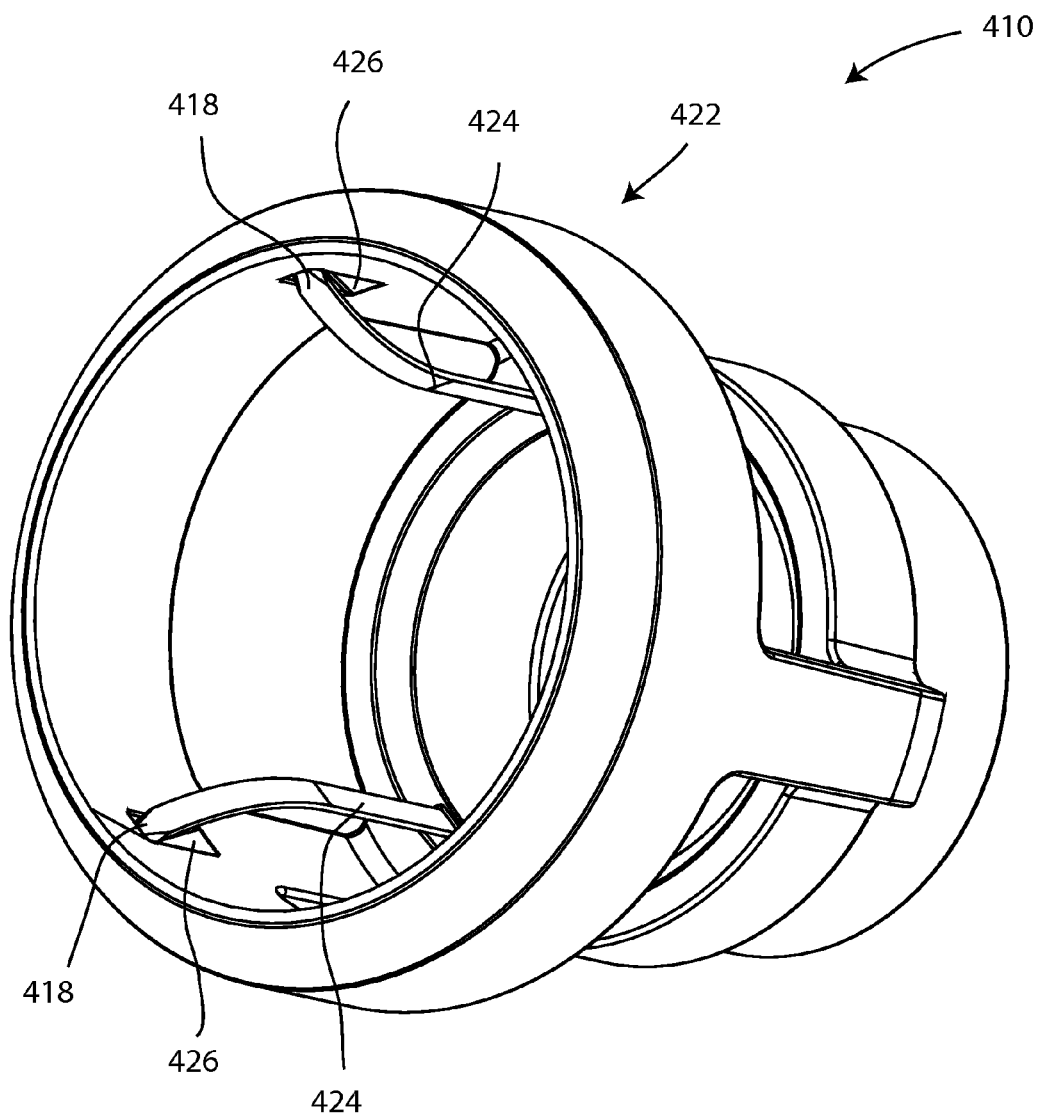
FIG. 17 is another perspective view of the tissue fixation device of FIG. 16 with the tissue fixation members in the deployed configuration.
Figure 18:
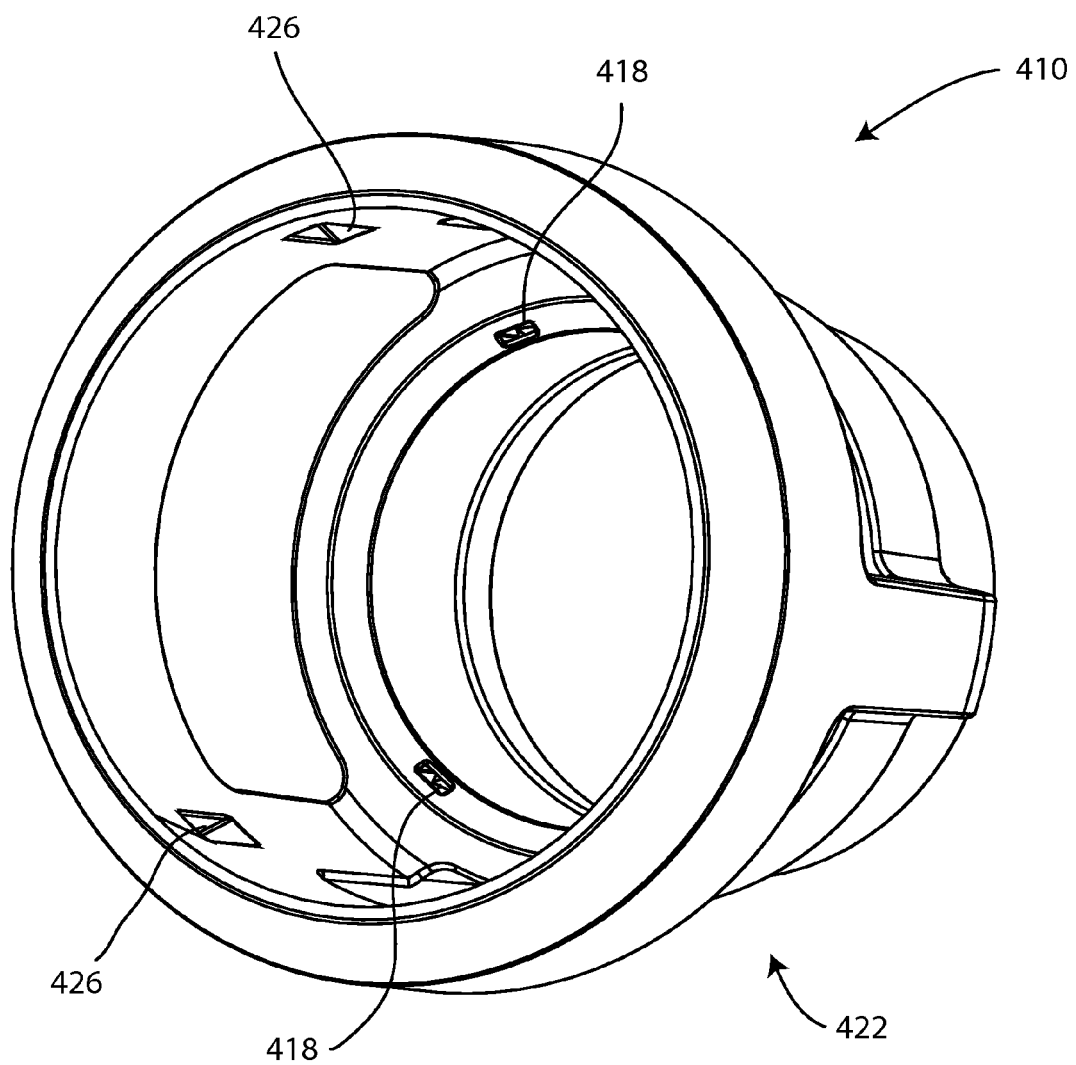
FIG. 18 is a perspective view of the tissue fixation device of FIG. 16 with the tissue fixation members in the retracted configuration.

FIGS. 16-18 show a tissue fixation device 420 having a housing 422 and at least one curved fixation member 424. In this embodiment there are three curved fixation members 424, however, other embodiments may include more or fewer curved fixation members 424. FIGS. 16 and 17 show the curved fixation members 424 in the deployed position and FIG. 18 shows the curved fixation members 424 in the retracted position. The curved fixation members 424 may be flexible, semi-flexible, or rigid. The curved fixation members 424 may be advanced upward from the housing 422, through tissue, and the tips 418 of the curved fixation members 424 may then be received in capture features 426 formed in the housing 422 to hold the tissue relative to the housing 422. Other embodiments may reverse the deployment direction of the curved fixation members 424. For example, the curved fixation members 424 may be advanced downward from the housing 422, through tissue, such that the tips 418 of the curved fixation members 424 are received in capture features 426 formed in the lower portion of the housing 422. In this embodiment, the position of the apertures where the curved fixation members 424 exit the housing and the capture features 426 are reversed. In other embodiments, the curved fixation members 424 may be advanced sideways from the housing 422 and into capture features 426 formed on the sides of the housing 422 such that the apertures where the curved fixation members 424 exit the housing and the capture features 426 lie in a plane substantially perpendicular to the lengthwise central axis of the housing 422.

Figure 19:
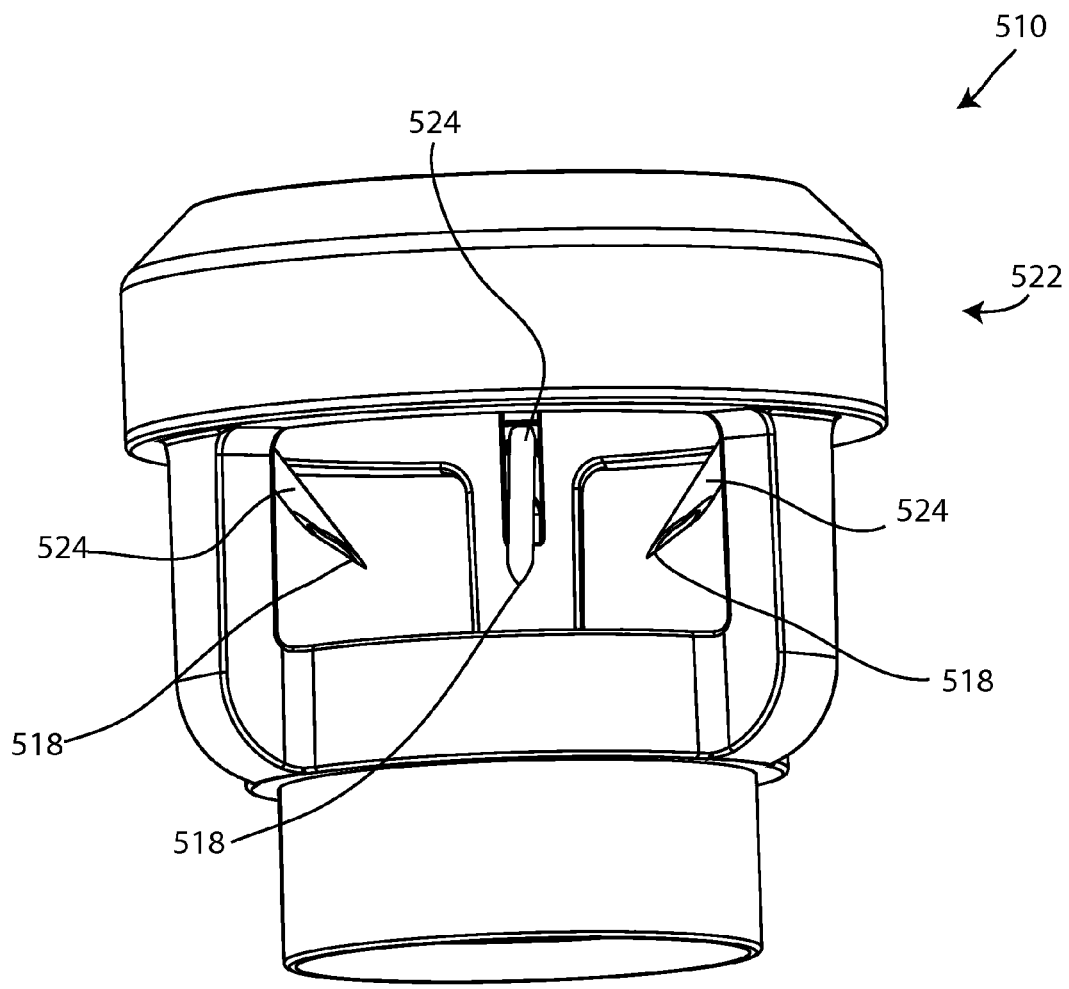
FIG. 19 is a perspective view of another tissue fixation device in accordance with the present disclosure with the tissue fixation members in the deployed configuration.
Figure 20:
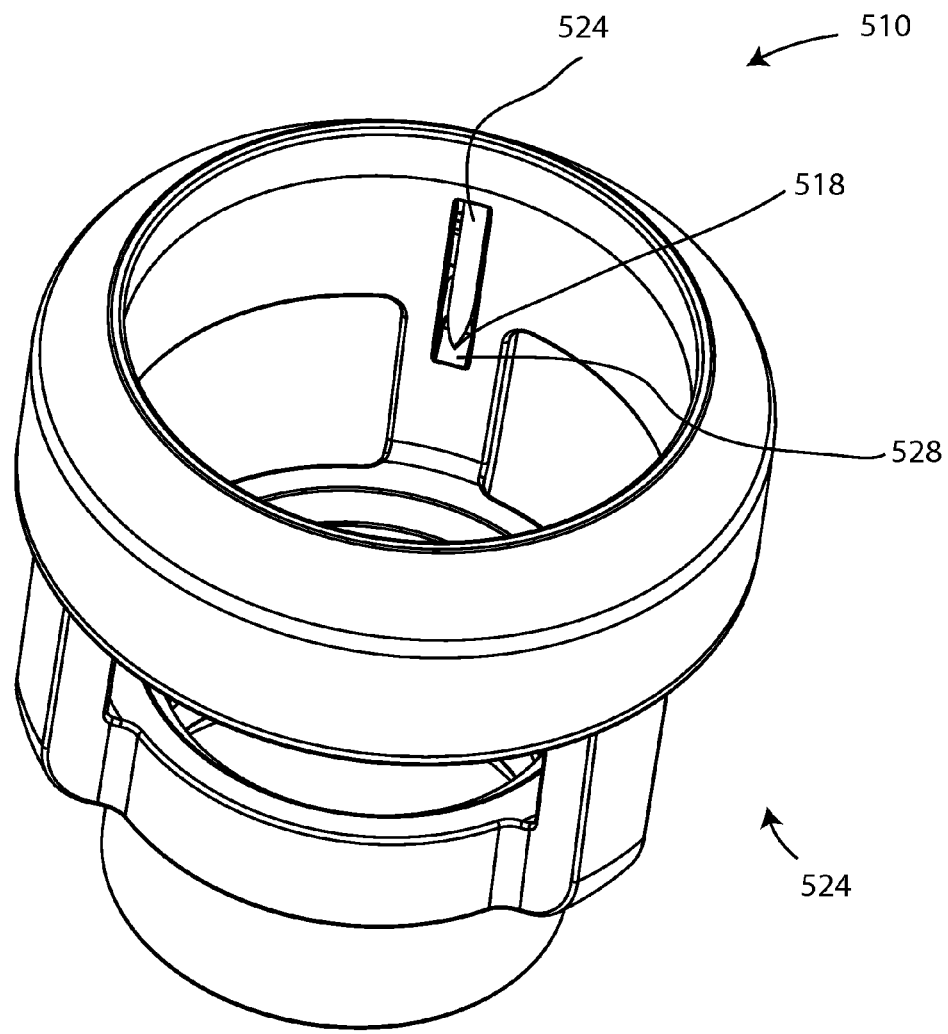
FIG. 20 is a perspective view of the tissue fixation device of FIG. 19 with the tissue fixation members in the retracted configuration.

FIGS. 19-20 show a tissue fixation device 510 having a housing 522 and one or more fixation members 524. In this example there are three fixation members, however in other examples there may be more or fewer fixation members 524. FIG. 19 shows the tissue fixation device 510 with the fixation members 524 in the deployed position. FIG. 20 shows the tissue fixation device 510 with the fixation members 524 in the retracted configuration. The housing can have angled ramps 528 formed near the beveled tips 518 of the fixation members 524 which force the fixation members toward the center of the tissue fixation device 510 and into the tissue as the fixation members 524 are moved into the deployed position. The fixation members 524 can be moved between the deployed and retracted positions by means discussed herein including sutures, levers, sliding tabs, translating members or any other suitable mechanical means.

It should be understood that the present apparatuses and methods are not intended to be limited to the particular forms disclosed. Rather, they are intended to include all modifications, equivalents, and alternatives falling within the scope of the claims. They are further intended to include embodiments which may be formed by combining features from the disclosed embodiments, and variants thereof.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as has and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, fixation members, needles, hooks or barbs may be interchangeable in any of the embodiments set forth herein, as may the actuation means for deployment. As such, the described embodiments are to be considered in all respects only as illustrative and not restrictive. Similarly, manufacturing, assembly methods, and materials described for one device may be used in the manufacture or assembly of another device. The scope of the invention is, therefore, indicated by the appended claims rather than by the foregoing description. All changes which come within the meaning and range of equivalency of the claims are to be embraced within their scope.

The invention claimed is:

1. A tissue fixation device, comprising:
   a housing having:
      an opening configured to receive tissue therein;
      an enclosed section bounded by an inner wall;
   at least two fixation members movable between a retracted configuration and a deployed configuration, each fixation member having a sharp point capable of piercing tissue, wherein when the fixation members are in the deployed configuration, the fixation members protrude through the inner wall into the opening, and wherein when the fixation members are in the retracted configuration, the fixation members are retracted relative to the opening;
   wherein the entirety of the fixation members lie within a single plane when in the deployed configuration and when in the retracted configuration;
   a fixation member carriage engaged with the fixation members and configured to move the fixation members between the deployed configuration and the retracted configuration; and
   a line having a first portion and a second portion, the line connected to the fixation member carriage, wherein pulling the first portion of the line moves the fixation member carriage in a first direction to deploy the fixation members, and wherein pulling the second portion of the line moves the fixation member carriage in a second direction to retract the fixation members.

2. The tissue fixation device of claim 1, wherein at least a portion of each fixation member diverges from a lengthwise central axis of the housing in the deployed configuration.

3. The tissue fixation device of claim 2, wherein each fixation member is curved with an arch shape that substantially lies in the single plane.

4. The tissue fixation device of claim 1, wherein the housing defines a lengthwise central axis, and wherein the single plane is perpendicular to the lengthwise central axis of the housing.

5. A method of fixing a tissue comprising:
   providing a tissue fixation device having:
      a housing:
         an opening configured to receive tissue therein; and
         an enclosed section;
      at least two fixation members movable between a retracted configuration and a deployed configuration, each fixation member having a sharp point capable of piercing tissue, wherein when the fixation members are in the deployed configuration, the fixation members protrude into the opening, and wherein when the fixation members are in the retracted configuration, the fixation members are retracted relative to the opening;
      a fixation member carriage engaged with the fixation members and configured to move the fixation members between the deployed configuration and the retracted configuration; and
      a line having a first portion and a second portion, the line connected to the fixation member carriage, wherein pulling the first portion of the line moves the fixation member carriage in a first direction to deploy the fixation members, and wherein pulling the second portion of the line moves the fixation member carriage in a second direction to retract the fixation members;
   inserting tissue into the opening of the housing; and
   selectively moving the fixation members exclusively along a single plane between the retracted configuration and the deployed configuration.

6. The method of claim 5, wherein at least a portion of each of the fixation members diverges from a lengthwise central axis of the housing in the deployed configuration.

7. The tissue fixation device of claim 6, wherein each fixation member is curved with an arch shape that lies substantially in a single plane.

8. The tissue fixation device of claim 5, wherein the housing defines a lengthwise central axis, and wherein the single plane is perpendicular to the lengthwise central axis of the housing.

9. The tissue fixation device of claim 5, wherein the enclosed section is bounded by an inner wall, and wherein moving the fixation members between the retracted configuration and the deployed configuration comprises moving the fixations members to protrude through the wall.

10. A tissue fixation device, comprising:
    a housing having:
       an opening, configured to receive tissue therein; and
       an inner wall surrounding the opening, the inner wall encircled by an outer rim;
    at least one fixation member movable between a retracted configuration and a deployed configuration, the at least one fixation member having a sharp point capable of piercing tissue, wherein when the at least one fixation member is in the deployed configuration, the at least one fixation member protrudes from the inner wall into the opening, and wherein when the at least one fixation member is in the retracted configuration, the at least one fixation member is retracted from the opening toward the inner surface, wherein the entirety of the at least one fixation member is captured between the inner wall and the outer rim when in the retracted configuration;
    a fixation member carriage engaged with the at least one fixation member and configured to move the at least one fixation member between the deployed configuration and the retracted configuration; and
    a line having a first portion and a second portion, the line connected to the fixation member carriage, wherein pulling the first portion of the line moves the fixation member carriage in a first direction to deploy the at least one fixation member, and wherein pulling the second portion of the line moves the fixation member carriage in a second direction to retract the at least one fixation member.

11. The tissue fixation device of claim 10, wherein at least a portion of the at least one fixation member diverges from a lengthwise central axis of the housing in the deployed configuration.

12. The tissue fixation device of claim 11, wherein the at least one fixation member is curved with an arch shape that substantially lies in a single plane.

* * * * *